(12) United States Patent
Sidar et al.

(10) Patent No.: US 10,130,246 B2
(45) Date of Patent: Nov. 20, 2018

(54) SYSTEMS AND METHODS FOR REGULATING TEMPERATURE AND ILLUMINATION INTENSITY AT THE DISTAL TIP OF AN ENDOSCOPE

(71) Applicant: EndoChoice, Inc., Alpharetta, GA (US)

(72) Inventors: Itay Sidar, Haifa (IL); Tal Davidson, Yokneam Ilit (IL); Achia Kronman, Pardes Hanna (IL); Yaniv Kirma, Karcur (IL); Yuri Gershov, Haifa (IL); Golan Salman, Atlit (IL)

(*) Notice: Subject to any disclaimer, the term of this patent is extended or adjusted under 35 U.S.C. 154(b) by 250 days.

(21) Appl. No.: 15/144,438

(22) Filed: May 2, 2016

(65) Prior Publication Data

US 2016/0345814 A1   Dec. 1, 2016

Related U.S. Application Data

(63) Continuation-in-part of application No. 14/274,323, filed on May 9, 2014, now Pat. No. 9,474,440, which is a continuation-in-part of application No. 13/984,028, filed as application No. PCT/IL2012/050037 on Feb. 6, 2012, now Pat. No.
(Continued)

(51) Int. Cl.
| | | |
|---|---|---|
| H04N 7/18 | (2006.01) | |
| H04N 9/47 | (2006.01) | |
| A62B 1/04 | (2006.01) | |
| A61B 1/12 | (2006.01) | |
| A61B 1/06 | (2006.01) | |
| A61B 1/00 | (2006.01) | |

(52) U.S. Cl.
CPC ............ *A61B 1/128* (2013.01); *A61B 1/0676* (2013.01); *A61B 1/0684* (2013.01); *A61B 1/00006* (2013.01)

(58) Field of Classification Search
None
See application file for complete search history.

(56) References Cited

U.S. PATENT DOCUMENTS

| | | | |
|---|---|---|---|
| 4,027,697 A | 6/1977 | Bonney | |
| 4,084,401 A | 4/1978 | Belardi | |
(Continued)

FOREIGN PATENT DOCUMENTS

| | | | |
|---|---|---|---|
| CA | 2297986 | 3/1999 | |
| CA | 2765559 | 12/2010 | |
(Continued)

OTHER PUBLICATIONS

Office Action dated Feb. 26, 2016 for U.S. Appl. No. 14/274,323.
(Continued)

*Primary Examiner* — Talha M Nawaz
(74) *Attorney, Agent, or Firm* — Bookoff McAndrews, PLLC

(57) ABSTRACT

The present specification describes a system and method for computing the temperature of the tip of a multiple viewing elements endoscope based on a measurement of junction temperatures of light emitting diode (LED) illuminators inside the tip. The measurement of temperature is used for taking corrective action if the temperature exceeds a limit. The temperature measurement is used for optimizing image parameters, as the performance of image sensors is affected by changes in ambient temperature.

10 Claims, 23 Drawing Sheets

Related U.S. Application Data 9,101,266, said application No. 14/274,323 is a continuation-in-part of application No. 13/992,021, filed as application No. PCT/IL2011/050050 on Dec. 8, 2011, now Pat. No. 9,320,419, said application No. 14/274,323 is a continuation-in-part of application No. 13/992,014, filed as application No. PCT/IL2011/050049 on Dec. 8, 2011, now Pat. No. 9,814,374, said application No. 14/274,323 is a continuation-in-part of application No. 13/882,004, filed as application No. PCT/IL2011/000832 on Oct. 27, 2011, now abandoned, said application No. 14/274,323 is a continuation-in-part of application No. 13/822,908, filed as application No. PCT/IL2011/000745 on Sep. 20, 2011, said application No. 14/274,323 is a continuation-in-part of application No. 13/713,449, filed on Dec. 13, 2012, now Pat. No. 9,655,502, and a continuation-in-part of application No. 13/655,120, filed on Oct. 18, 2012, now Pat. No. 9,872,609, which is a continuation-in-part of application No. 13/119,032, filed as application No. PCT/IL2010/000476 on Jun. 16, 2010, now Pat. No. 9,554,692, said application No. 14/274,323 is a continuation-in-part of application No. 13/212,627, filed on Aug. 18, 2011, now Pat. No. 9,492,063, which is a continuation-in-part of application No. 13/119,032, filed on Jul. 15, 2011, now Pat. No. 9,554,692, said application No. 14/274,323 is a continuation-in-part of application No. 13/190,968, filed on Jul. 26, 2011, now Pat. No. 9,101,268, which is a continuation-in-part of application No. 13/119,032, filed on Jul. 15, 2011, now Pat. No. 9,554,692, said application No. 14/274,323 is a continuation-in-part of application No. 13/413,252, filed on Mar. 6, 2012, now Pat. No. 9,101,287, and a continuation-in-part of application No. 13/413,141, filed on Mar. 6, 2012, now Pat. No. 8,926,502, and a continuation-in-part of application No. 13/413,059, filed on Mar. 6, 2012, now Pat. No. 9,402,533, and a continuation-in-part of application No. 13/412,974, filed on Mar. 6, 2012, now abandoned.

(60) Provisional application No. 62/156,418, filed on May 4, 2015, provisional application No. 62/235,768, filed on Oct. 1, 2015, provisional application No. 61/822,805, filed on May 13, 2013, provisional application No. 61/439,948, filed on Feb. 7, 2011, provisional application No. 61/421,240, filed on Dec. 9, 2010, provisional application No. 61/421,238, filed on Dec. 9, 2010, provisional application No. 61/407,495, filed on Oct. 28, 2010, provisional application No. 61/384,354, filed on Sep. 20, 2010, provisional application No. 61/569,796, filed on Dec. 13, 2011, provisional application No. 61/218,085, filed on Jun. 18, 2009, provisional application No. 61/449,746, filed on Mar. 7, 2011, provisional application No. 61/449,743, filed on Mar. 7, 2011, provisional application No. 61/449,741, filed on Mar. 7, 2011, provisional application No. 61/449,739, filed on Mar. 7, 2011.

(56) References Cited

U.S. PATENT DOCUMENTS

| | | | |
|---|---|---|---|
| 4,402,313 | A | 9/1983 | Yabe |
| 4,461,282 | A | 7/1984 | Ouchi |
| 4,494,549 | A | 1/1985 | Namba |
| 4,532,918 | A | 8/1985 | Wheeler |
| 4,588,294 | A | 5/1986 | Siegmund |
| 4,641,635 | A | 2/1987 | Yabe |
| 4,727,859 | A | 3/1988 | Lia |
| 4,764,001 | A | 8/1988 | Yokota |
| 4,801,792 | A | 1/1989 | Yamasita |
| 4,825,850 | A | 5/1989 | Opie |
| 4,877,314 | A | 10/1989 | Kanamori |
| 4,902,115 | A | 2/1990 | Takahashi |
| 4,976,522 | A | 12/1990 | Igarashi |
| 4,984,878 | A | 1/1991 | Miyano |
| 5,007,406 | A | 4/1991 | Takahashi |
| 5,014,685 | A | 5/1991 | Takahashi |
| 5,193,525 | A | 3/1993 | Silverstein |
| 5,224,929 | A | 7/1993 | Remiszewski |
| 5,296,971 | A | 3/1994 | Mori |
| 5,359,456 | A | 10/1994 | Kikuchi |
| 5,395,329 | A | 3/1995 | Fleischhacker |
| 5,447,148 | A | 9/1995 | Oneda |
| 5,460,167 | A | 10/1995 | Yabe |
| 5,464,007 | A | 11/1995 | Krauter |
| 5,489,256 | A | 2/1996 | Adair |
| 5,518,501 | A | 5/1996 | Oneda |
| 5,518,502 | A | 5/1996 | Kaplan |
| 5,547,457 | A | 8/1996 | Tsuyuki |
| 5,575,755 | A | 11/1996 | Krauter |
| 5,587,839 | A | 12/1996 | Miyano |
| 5,630,782 | A | 5/1997 | Adair |
| 5,662,588 | A | 9/1997 | Iida |
| 5,674,182 | A | 10/1997 | Suzuki |
| 5,685,823 | A | 11/1997 | Ito |
| 5,702,347 | A | 12/1997 | Yabe |
| 5,707,344 | A | 1/1998 | Nakazawa |
| 5,725,474 | A | 3/1998 | Yasui |
| 5,725,476 | A | 3/1998 | Yasui |
| 5,725,477 | A | 3/1998 | Yasui |
| 5,725,478 | A | 3/1998 | Saad |
| 5,777,797 | A | 7/1998 | Miyano |
| 5,782,751 | A | 7/1998 | Matsuno |
| 5,810,715 | A | 9/1998 | Moriyama |
| 5,836,894 | A | 11/1998 | Sarvazyan |
| 5,860,913 | A | 1/1999 | Yamaya |
| 5,870,234 | A | 2/1999 | EbbesmeierneeSchitthof |
| 5,916,148 | A | 6/1999 | Tsuyuki |
| 5,940,126 | A | 8/1999 | Kimura |
| 6,095,970 | A | 8/2000 | Hidaka |
| 6,117,068 | A | 9/2000 | Gourley |
| 6,181,481 | B1 | 1/2001 | Yamamoto |
| 6,196,967 | B1 | 3/2001 | Lim |
| 6,261,226 | B1 | 7/2001 | McKenna |
| 6,277,064 | B1 | 8/2001 | Yoon |
| 6,359,674 | B1 | 3/2002 | Horiuchi |
| 6,375,610 | B2 | 4/2002 | Verschuur |
| 6,402,738 | B1 | 6/2002 | Ouchi |
| 6,419,626 | B1 | 7/2002 | Yoon |
| 6,476,851 | B1 | 11/2002 | Nakamura |
| 6,638,214 | B2 | 10/2003 | Akiba |
| 6,673,012 | B2 | 1/2004 | Fujii |
| 6,712,760 | B2 | 3/2004 | Sano |
| 6,832,984 | B2 | 12/2004 | Stelzer |
| 6,888,119 | B2 | 5/2005 | Iizuka |
| 7,435,218 | B2 | 10/2008 | Krattiger |
| 7,621,869 | B2 | 11/2009 | Ratnakar |
| 7,630,148 | B1 | 12/2009 | Yang |
| 7,701,650 | B2 | 4/2010 | Lin |
| 7,713,246 | B2 | 5/2010 | Shia |
| 7,746,572 | B2 | 6/2010 | Asami |
| 7,813,047 | B2 | 10/2010 | Wang |
| 7,828,725 | B2 | 11/2010 | Maruyama |
| 7,927,272 | B2 | 4/2011 | Bayer |
| 7,967,745 | B2 | 6/2011 | Gilad |
| 7,976,462 | B2 | 7/2011 | Wright |
| 8,064,666 | B2 | 11/2011 | Bayer |
| 8,182,422 | B2 | 5/2012 | Bayer |
| 8,197,399 | B2 | 6/2012 | Bayer |
| 8,235,887 | B2 | 8/2012 | Bayer |
| 8,262,558 | B2 | 9/2012 | Sato |
| 8,287,446 | B2 | 10/2012 | Bayer |

(56) References Cited

U.S. PATENT DOCUMENTS

| | | | |
|---|---|---|---|
| 8,289,381 B2 | 10/2012 | Bayer |
| 8,300,325 B2 | 10/2012 | Katahira |
| 8,310,530 B2 | 11/2012 | Bayer |
| 8,447,132 B1 | 5/2013 | Galil |
| 8,449,457 B2 | 5/2013 | Aizenfeld |
| 8,585,584 B2 | 11/2013 | Ratnakar |
| 8,587,645 B2 | 11/2013 | Bayer |
| 8,672,836 B2 | 3/2014 | Higgins |
| 8,715,168 B2 | 5/2014 | Ratnakar |
| 8,797,392 B2 | 8/2014 | Bayer |
| 8,872,906 B2 | 10/2014 | Bayer |
| 8,926,502 B2 | 1/2015 | Levy |
| 9,044,185 B2 | 6/2015 | Bayer |
| 9,101,266 B2 | 8/2015 | Levi |
| 9,101,268 B2 | 8/2015 | Levy |
| 9,101,287 B2 | 8/2015 | Levy |
| 9,314,147 B2 | 4/2016 | Levy |
| 9,320,419 B2 | 4/2016 | Kirma |
| 2001/0036322 A1 | 11/2001 | Bloomfield |
| 2002/0017515 A1 | 2/2002 | Obata |
| 2002/0047897 A1 | 4/2002 | Sugimoto |
| 2002/0087047 A1 | 7/2002 | Remijan |
| 2002/0109774 A1 | 8/2002 | Meron |
| 2002/0161281 A1 | 10/2002 | Jaffe |
| 2002/0172498 A1 | 11/2002 | Esenyan |
| 2002/0183591 A1 | 12/2002 | Matsuura |
| 2003/0030918 A1 | 2/2003 | Murayama |
| 2003/0063398 A1 | 4/2003 | Abe |
| 2003/0076411 A1 | 4/2003 | Iida |
| 2003/0083552 A1 | 5/2003 | Remijan |
| 2003/0128893 A1 | 7/2003 | Castorina |
| 2003/0153897 A1 | 8/2003 | Russo |
| 2004/0015054 A1 | 1/2004 | Hino |
| 2004/0046865 A1 | 3/2004 | Ueno |
| 2004/0061780 A1 | 4/2004 | Huffman |
| 2004/0106850 A1 | 6/2004 | Yamaya |
| 2004/0133072 A1 | 7/2004 | Kennedy |
| 2004/0138532 A1 | 7/2004 | Glukhovsky |
| 2004/0158129 A1 | 8/2004 | Okada |
| 2004/0160682 A1 | 8/2004 | Miyano |
| 2004/0190159 A1 | 9/2004 | Hasegawa |
| 2004/0193010 A1 | 9/2004 | Fujimori et al. |
| 2004/0249247 A1 | 12/2004 | Iddan |
| 2005/0018042 A1 | 1/2005 | Rovegno |
| 2005/0020876 A1 | 1/2005 | Shioda |
| 2005/0038317 A1 | 2/2005 | Ratnakar |
| 2005/0047134 A1 | 3/2005 | Mueller |
| 2005/0090709 A1 | 4/2005 | Okada |
| 2005/0096501 A1 | 5/2005 | Stelzer |
| 2005/0119527 A1 | 6/2005 | Banik |
| 2005/0234296 A1 | 10/2005 | Saadat |
| 2005/0234347 A1 | 10/2005 | Yamataka |
| 2005/0251127 A1 | 11/2005 | Brosch |
| 2005/0272975 A1 | 12/2005 | McWeeney |
| 2005/0283048 A1 | 12/2005 | Gill |
| 2006/0047184 A1 | 3/2006 | Banik |
| 2006/0063976 A1 | 3/2006 | Aizenfeld |
| 2006/0069314 A1 | 3/2006 | Farr |
| 2006/0114986 A1 | 6/2006 | Knapp |
| 2006/0149129 A1 | 7/2006 | Watts |
| 2006/0171693 A1* | 8/2006 | Todd .................. A61B 1/00029 396/17 |
| 2006/0173245 A1* | 8/2006 | Todd .................. A61B 1/0653 600/178 |
| 2006/0183975 A1 | 8/2006 | Saadat |
| 2006/0184037 A1 | 8/2006 | Ince |
| 2006/0189845 A1 | 8/2006 | Maahs |
| 2006/0215406 A1 | 9/2006 | Thrailkill |
| 2006/0252994 A1 | 11/2006 | Ratnakar |
| 2006/0264704 A1 | 11/2006 | Fujimori |
| 2006/0293556 A1 | 12/2006 | Garner |
| 2007/0015989 A1 | 1/2007 | Desai |
| 2007/0049803 A1 | 3/2007 | Moriyama |
| 2007/0055100 A1 | 3/2007 | Kato |
| 2007/0079029 A1 | 4/2007 | Carlson |
| 2007/0088193 A1 | 4/2007 | Omori |
| 2007/0106119 A1 | 5/2007 | Hirata |
| 2007/0142711 A1 | 6/2007 | Bayer |
| 2007/0162095 A1 | 7/2007 | Kimmel |
| 2007/0167681 A1 | 7/2007 | Gill |
| 2007/0177008 A1 | 8/2007 | Bayer |
| 2007/0177009 A1 | 8/2007 | Bayer |
| 2007/0185384 A1 | 8/2007 | Bayer |
| 2007/0188427 A1 | 8/2007 | Lys |
| 2007/0197875 A1 | 8/2007 | Osaka |
| 2007/0203396 A1 | 8/2007 | McCutcheon |
| 2007/0206945 A1 | 9/2007 | Delorme |
| 2007/0213591 A1 | 9/2007 | Aizenfeld |
| 2007/0229656 A1 | 10/2007 | Khait |
| 2007/0244353 A1 | 10/2007 | Larsen |
| 2007/0244354 A1 | 10/2007 | Bayer |
| 2007/0247867 A1 | 10/2007 | Hunter |
| 2007/0249907 A1* | 10/2007 | Boulais ................. A61B 1/0008 600/179 |
| 2007/0265492 A1 | 11/2007 | Sonnenschein |
| 2007/0270642 A1 | 11/2007 | Bayer |
| 2007/0279486 A1 | 12/2007 | Bayer |
| 2007/0293720 A1 | 12/2007 | Bayer |
| 2008/0021274 A1 | 1/2008 | Bayer |
| 2008/0025413 A1 | 1/2008 | Apostolopoulos |
| 2008/0036864 A1 | 2/2008 | McCubbrey |
| 2008/0045797 A1 | 2/2008 | Yasushi |
| 2008/0058601 A1 | 3/2008 | Fujimori |
| 2008/0071290 A1 | 3/2008 | Larkin |
| 2008/0130108 A1 | 6/2008 | Bayer |
| 2008/0151070 A1 | 6/2008 | Shiozawa |
| 2008/0161646 A1 | 7/2008 | Gomez |
| 2008/0163652 A1 | 7/2008 | Shatskin |
| 2008/0167529 A1 | 7/2008 | Otawara |
| 2008/0177139 A1 | 7/2008 | Courtney |
| 2008/0183034 A1 | 7/2008 | Henkin |
| 2008/0183043 A1 | 7/2008 | Spinnler |
| 2008/0221388 A1 | 7/2008 | Courtney |
| 2008/0253686 A1 | 10/2008 | Bayer |
| 2008/0262312 A1 | 10/2008 | Carroll |
| 2008/0275298 A1 | 11/2008 | Ratnakar |
| 2008/0303898 A1 | 12/2008 | Nishimura |
| 2009/0005643 A1 | 1/2009 | Smith |
| 2009/0023998 A1 | 1/2009 | Ratnakar |
| 2009/0030275 A1 | 1/2009 | Nicolaou |
| 2009/0054790 A1 | 2/2009 | Czaniera |
| 2009/0062615 A1 | 3/2009 | Yamaya |
| 2009/0086017 A1 | 4/2009 | Miyano |
| 2009/0135245 A1 | 5/2009 | Luo |
| 2009/0137875 A1 | 5/2009 | Kitagawa |
| 2009/0143647 A1 | 6/2009 | Banju |
| 2009/0147076 A1 | 6/2009 | Ertas |
| 2009/0182917 A1 | 7/2009 | Kim |
| 2009/0213211 A1 | 8/2009 | Bayer |
| 2009/0216084 A1 | 8/2009 | Yamane |
| 2009/0231419 A1 | 9/2009 | Bayer |
| 2009/0234183 A1 | 9/2009 | Abe |
| 2009/0253966 A1 | 10/2009 | Ichimura |
| 2009/0287188 A1 | 11/2009 | Golden |
| 2009/0287192 A1 | 11/2009 | Vivenzio |
| 2009/0299144 A1 | 12/2009 | Shigemori |
| 2010/0010309 A1 | 1/2010 | Kitagawa |
| 2010/0016673 A1 | 1/2010 | Bandy |
| 2010/0053312 A1 | 3/2010 | Watanabe |
| 2010/0060861 A1* | 3/2010 | Medin .................. G03B 21/16 353/57 |
| 2010/0069713 A1 | 3/2010 | Endo |
| 2010/0073470 A1 | 3/2010 | Takasaki |
| 2010/0073948 A1 | 3/2010 | Stein |
| 2010/0076268 A1 | 3/2010 | Takasugi |
| 2010/0123950 A1 | 5/2010 | Fujiwara |
| 2010/0130822 A1 | 5/2010 | Katayama |
| 2010/0141763 A1 | 6/2010 | Itoh |
| 2010/0160729 A1 | 6/2010 | Smith |
| 2010/0174144 A1 | 7/2010 | Hsu |
| 2010/0231702 A1 | 9/2010 | Tsujimura |
| 2010/0245653 A1 | 9/2010 | Bodor |
| 2010/0249513 A1 | 9/2010 | Tydlaska |
| 2010/0280322 A1 | 11/2010 | Mizuyoshi |

(56) References Cited

U.S. PATENT DOCUMENTS

| | | |
|---|---|---|
| 2010/0296178 A1 | 11/2010 | Genet |
| 2011/0031903 A1 | 2/2011 | Nguyen et al. |
| 2011/0034769 A1 | 2/2011 | Adair |
| 2011/0063427 A1 | 3/2011 | Fengler |
| 2011/0140003 A1 | 6/2011 | Beck |
| 2011/0160530 A1 | 6/2011 | Ratnakar |
| 2011/0160535 A1 | 6/2011 | Bayer |
| 2011/0169931 A1 | 7/2011 | Pascal |
| 2011/0184243 A1 | 7/2011 | Wright |
| 2011/0211267 A1 | 9/2011 | Takato |
| 2011/0263938 A1 | 10/2011 | Levy |
| 2011/0282144 A1 | 11/2011 | Gettman |
| 2011/0292258 A1 | 12/2011 | Adler |
| 2012/0040305 A1 | 2/2012 | Karazivan |
| 2012/0050606 A1 | 3/2012 | Debevec |
| 2012/0053407 A1 | 3/2012 | Levy |
| 2012/0057251 A1 | 3/2012 | Takato |
| 2012/0065468 A1 | 3/2012 | Levy |
| 2012/0076425 A1 | 3/2012 | Brandt |
| 2012/0209071 A1 | 8/2012 | Bayer |
| 2012/0209289 A1 | 8/2012 | Duque |
| 2012/0212630 A1 | 8/2012 | Pryor |
| 2012/0220832 A1 | 8/2012 | Nakade |
| 2012/0224026 A1 | 9/2012 | Bayer |
| 2012/0229615 A1 | 9/2012 | Kirma |
| 2012/0232340 A1 | 9/2012 | Levy |
| 2012/0232343 A1 | 9/2012 | Levy |
| 2012/0253121 A1 | 10/2012 | Kitano |
| 2012/0277535 A1 | 11/2012 | Hoshino |
| 2012/0299481 A1 | 11/2012 | Stevens |
| 2012/0300999 A1 | 11/2012 | Bayer |
| 2013/0030248 A1 | 1/2013 | Matsumaru |
| 2013/0053646 A1 | 2/2013 | Yamamoto |
| 2013/0057724 A1 | 3/2013 | Miyahara |
| 2013/0066297 A1 | 3/2013 | Shtul |
| 2013/0085329 A1 | 4/2013 | Morrissette |
| 2013/0109916 A1 | 5/2013 | Levy |
| 2013/0116506 A1 | 5/2013 | Bayer |
| 2013/0131447 A1 | 5/2013 | Benning |
| 2013/0137930 A1 | 5/2013 | Menabde |
| 2013/0150671 A1 | 6/2013 | Levy |
| 2013/0169843 A1 | 7/2013 | Ono |
| 2013/0172670 A1 | 7/2013 | Levy |
| 2013/0172676 A1 | 7/2013 | Levy |
| 2013/0197309 A1 | 8/2013 | Sakata |
| 2013/0197556 A1 | 8/2013 | Shelton |
| 2013/0222640 A1 | 8/2013 | Baek |
| 2013/0264465 A1 | 10/2013 | Dai |
| 2013/0267778 A1 | 10/2013 | Rehe |
| 2013/0271588 A1 | 10/2013 | Kirma |
| 2013/0274551 A1 | 10/2013 | Kirma |
| 2013/0281925 A1 | 10/2013 | Benscoter |
| 2013/0296649 A1 | 11/2013 | Kirma |
| 2013/0303979 A1 | 11/2013 | Stieglitz |
| 2013/0317295 A1 | 11/2013 | Morse |
| 2014/0018624 A1 | 1/2014 | Bayer |
| 2014/0031627 A1 | 1/2014 | Jacobs |
| 2014/0046136 A1 | 2/2014 | Bayer |
| 2014/0107418 A1 | 4/2014 | Ratnakar |
| 2014/0148644 A1 | 5/2014 | Levi |
| 2014/0213850 A1 | 7/2014 | Levy |
| 2014/0225998 A1 | 8/2014 | Dai |
| 2014/0276207 A1 | 9/2014 | Ouyang |
| 2014/0296628 A1 | 10/2014 | Kirma |
| 2014/0296643 A1 | 10/2014 | Levy |
| 2014/0296866 A1 | 10/2014 | Salman |
| 2014/0309495 A1 | 10/2014 | Kirma |
| 2014/0316198 A1 | 10/2014 | Krivopisk |
| 2014/0316204 A1 | 10/2014 | Ofir |
| 2014/0320617 A1 | 10/2014 | Parks |
| 2014/0333742 A1 | 11/2014 | Salman |
| 2014/0333743 A1 | 11/2014 | Gilreath |
| 2014/0336459 A1 | 11/2014 | Bayer |
| 2014/0343358 A1 | 11/2014 | Hameed |
| 2014/0343361 A1 | 11/2014 | Salman |
| 2014/0343489 A1 | 11/2014 | Lang |
| 2014/0364691 A1 | 12/2014 | Krivopisk |
| 2014/0364692 A1 | 12/2014 | Salman |
| 2014/0364694 A1 | 12/2014 | Avron |
| 2015/0005581 A1 | 1/2015 | Salman |
| 2015/0045614 A1 | 2/2015 | Krivopisk |
| 2015/0057500 A1 | 2/2015 | Salman |
| 2015/0094536 A1 | 4/2015 | Wieth |
| 2015/0099925 A1 | 4/2015 | Davidson |
| 2015/0099926 A1 | 4/2015 | Davidson |
| 2015/0105618 A1 | 4/2015 | Levy |
| 2015/0164308 A1 | 6/2015 | Ratnakar |
| 2015/0182105 A1 | 7/2015 | Salman |
| 2015/0196190 A1 | 7/2015 | Levy |
| 2015/0201827 A1 | 7/2015 | Sidar |
| 2015/0208900 A1 | 7/2015 | Vidas |
| 2015/0208909 A1 | 7/2015 | Davidson |
| 2015/0223676 A1 | 8/2015 | Bayer |
| 2015/0230698 A1 | 8/2015 | Cline |
| 2015/0305601 A1 | 10/2015 | Levi |
| 2015/0313445 A1 | 11/2015 | Davidson |
| 2015/0313450 A1 | 11/2015 | Wieth |
| 2015/0313451 A1 | 11/2015 | Salman |
| 2015/0320300 A1 | 11/2015 | Gershov |
| 2015/0342446 A1 | 12/2015 | Levy |
| 2015/0359415 A1 | 12/2015 | Lang |
| 2015/0374206 A1 | 12/2015 | Shimony |
| 2016/0015257 A1 | 1/2016 | Levy |
| 2016/0015258 A1 | 1/2016 | Levin |
| 2016/0058268 A1 | 3/2016 | Salman |

FOREIGN PATENT DOCUMENTS

| | | |
|---|---|---|
| CA | 2812097 | 3/2012 |
| CA | 2798716 | 6/2013 |
| CA | 2798729 | 6/2013 |
| CN | 103348470 | 10/2013 |
| CN | 103403605 | 11/2013 |
| CN | 103491854 | 1/2014 |
| CN | 103702604 | 4/2014 |
| CN | 103732120 | 4/2014 |
| CN | 104717916 | 6/2015 |
| CN | 105246393 | 1/2016 |
| CN | 105324065 | 2/2016 |
| CN | 105324066 | 2/2016 |
| CN | 105338875 | 2/2016 |
| CN | 105358042 | 2/2016 |
| CN | 105358043 | 2/2016 |
| CN | 105377106 | 3/2016 |
| CN | 105407788 | 3/2016 |
| DE | 202010016900 | 5/2011 |
| EP | 1690497 | 8/2006 |
| EP | 1835844 | 9/2007 |
| EP | 1968425 | 9/2008 |
| EP | 1986541 | 11/2008 |
| EP | 1988813 | 11/2008 |
| EP | 2023794 | 2/2009 |
| EP | 2023795 | 2/2009 |
| EP | 2190341 | 6/2010 |
| EP | 2211683 | 8/2010 |
| EP | 2457492 | 5/2012 |
| EP | 2457493 | 5/2012 |
| EP | 1988812 | 11/2012 |
| EP | 2520218 | 11/2012 |
| EP | 2604175 | 6/2013 |
| EP | 2618718 | 7/2013 |
| EP | 2635932 | 9/2013 |
| EP | 2648602 | 10/2013 |
| EP | 2649648 | 10/2013 |
| EP | 2672878 | 12/2013 |
| EP | 2736400 | 6/2014 |
| EP | 2744390 | 6/2014 |
| EP | 2442706 | 11/2014 |
| EP | 2865322 | 4/2015 |
| EP | 2908714 | 8/2015 |
| EP | 2979123 | 2/2016 |
| EP | 2991537 | 3/2016 |
| EP | 2994032 | 3/2016 |
| EP | 2994033 | 3/2016 |

(56) References Cited

FOREIGN PATENT DOCUMENTS

| | | |
|---|---|---|
| EP | 2994034 | 3/2016 |
| EP | 2996536 | 3/2016 |
| EP | 2996541 | 3/2016 |
| EP | 2996542 | 3/2016 |
| EP | 2996621 | 3/2016 |
| GB | 12196628 | 3/2015 |
| JP | H1043129 | 2/1998 |
| JP | H10239740 | 9/1998 |
| JP | 11137512 | 5/1999 |
| JP | 2005253543 | 9/2005 |
| JP | 2006025888 | 2/2006 |
| JP | 2006068109 | 3/2006 |
| JP | 2010178766 A | 8/2010 |
| JP | 2012135432 | 7/2012 |
| JP | 2013116277 A2 | 6/2013 |
| JP | 2013123647 | 6/2013 |
| JP | 2013123648 | 6/2013 |
| JP | 2013208459 | 10/2013 |
| JP | 2013215582 | 10/2013 |
| JP | 2013230383 | 11/2013 |
| JP | 2013542467 | 11/2013 |
| JP | 2013544617 | 12/2013 |
| JP | 2014524303 | 9/2014 |
| JP | 2014524819 | 9/2014 |
| JP | 2015533300 | 11/2015 |
| WO | 2006073676 | 7/2006 |
| WO | 2006073725 | 7/2006 |
| WO | 2007070644 | 6/2007 |
| WO | 2007092533 | 8/2007 |
| WO | 2007092636 | 8/2007 |
| WO | 2007087421 | 11/2007 |
| WO | 2007136859 | 11/2007 |
| WO | 2007136879 | 11/2007 |
| WO | 2008015164 | 2/2008 |
| WO | 2009014895 | 1/2009 |
| WO | 2009015396 | 1/2009 |
| WO | 2009049322 | 4/2009 |
| WO | 2009049324 | 4/2009 |
| WO | 2009062179 | 5/2009 |
| WO | 2010146587 | 12/2010 |
| WO | 2012038958 | 3/2012 |
| WO | 2012056453 | 5/2012 |
| WO | 2012075153 A2 | 6/2012 |
| WO | 2012077116 | 6/2012 |
| WO | 2012077117 | 6/2012 |
| WO | 2012096102 | 7/2012 |
| WO | 2012120507 | 9/2012 |
| WO | 2013014673 | 1/2013 |
| WO | 2013024476 | 2/2013 |
| WO | 2014061023 | 4/2014 |
| WO | 2014160983 | 10/2014 |
| WO | 2014179236 | 11/2014 |
| WO | 2014182723 | 11/2014 |
| WO | 2014182728 | 11/2014 |
| WO | 2014183012 | 11/2014 |
| WO | 2014186230 | 11/2014 |
| WO | 2014186519 | 11/2014 |
| WO | 2014186521 | 11/2014 |
| WO | 2014186525 | 11/2014 |
| WO | 2014186775 | 11/2014 |
| WO | 2014210516 | 12/2014 |
| WO | 2015002847 | 1/2015 |
| WO | 2015047631 | 4/2015 |
| WO | 2015050829 | 4/2015 |
| WO | 2015084442 | 6/2015 |
| WO | 2015095481 | 6/2015 |
| WO | 2015112747 | 7/2015 |
| WO | 2015112899 | 7/2015 |
| WO | 2015134060 | 9/2015 |
| WO | 2015168066 | 11/2015 |
| WO | 2015168664 | 11/2015 |
| WO | 2015171732 | 11/2015 |
| WO | 2015175246 | 11/2015 |
| WO | 2016014581 | 1/2016 |
| WO | 2016033403 | 3/2016 |

OTHER PUBLICATIONS

Office Action dated Feb. 4, 2016 for U.S. Appl. No. 14/271,234.
International Search Report for PCT/US14/37004, dated Sep. 25, 2014.
International Search Report for PCT/US2014/037526, dated Oct. 16, 2014.
International Search Report for PCT/US14/38094, dated Nov. 6, 2014.
International Search Report for PCT/US2015/012751, dated Jun. 26, 2015.
International Search Report for PCT/US2014/58143, dated Jan. 21, 2015.
International Search Report for PCT/US2014/071085, dated Mar. 27, 2015.
International Search Report for PCT/US2015/027902, dated Jul. 23, 2015.
International Search Report for PCT/US2015/012506, dated Dec. 11, 2015.
International Search Report for PCT/US2015/29421, dated Aug. 7, 2015.
International Search Report for PCT/US2015/28962, dated Jul. 28, 2015.
International Search Report for PCT/US2015/47334, dated Dec. 28, 2015.
International Search Report for PCT/US2015/41396, dated Sep. 29, 2015.
International Search Report for PCT/US2015/66486, dated Dec. 17, 2015.
International Search Report for PCT/US2015/6548, dated Feb. 26, 2016.
Corrected Notice of Allowance dated Apr. 13, 2016 for U.S. Appl. No. 13/680,646.
Notice of Allowance dated Mar. 28, 2016 for U.S. Appl. No. 13/413,059.
Notice of Allowance dated Mar. 29, 2016 for U.S. Appl. No. 13/680,646.
Office Action dated Mar. 23, 2016 for U.S. Appl. No. 13/713,449.
Office Action dated Mar. 24, 2016 for U.S. Appl. No. 13/212,627.
Office Action dated Mar. 28, 2016 for U.S. Appl. No. 13/119,032.
Office Action dated May 25, 2016 for U.S. Appl. No. 14/271,234.
Office Action dated May 5, 2016 for U.S. Appl. No. 14/278,338.
Office Action dated May 6, 2016 for U.S. Appl. No. 14/263,896.

* cited by examiner

Table-II — Time-Surface Temperature Thresholds for Thermal Injury of Porcine Skin
MORITZ AND HENRIQUES

| Temperature in °C | Time (Minutes) | Time (Seconds) | Number of experiments | Hyperemia only — Mild | Hyperemia only — Severe | Focal epidermal necrosis — Scaling | Focal epidermal necrosis — Small ulcers | Complete epidermal necrosis — Red Burn | Complete epidermal necrosis — Pale Burn |
|---|---|---|---|---|---|---|---|---|---|
| 44 | 420 | | 1 | X | | | | | |
| 45 | 150 | | 1 | X | | | | X | |
| 45 | 180 | | 1 | X | | | | | |
| 46 | 45 | | 1 | X | | | | | |
| 46 | 60 | | 1 | X | | | | | |
| 46 | 90 | | 1 | | | | | X | |
| 46.5 | 45 | | 1 | X | | | | | |
| 46.5 | 60 | | 1 | | | | | X | |
| 47 | 35 | | 1 | X | | | | | |
| 47 | 45 | | 3 | | X | | | X X X | |
| 47 | 50 | | 1 | | | | | | |
| 47 | 60 | | 2 | | X | X | | | |
| 48 | 10 | | 2 | | X | | | X X | |
| 48 | 12 | | 1 | | | | | | |
| 48 | 14 | | 2 | | | | | X X | |
| 48 | 15 | | 1 | | | | | | |
| 48 | 16 | | 1 | | | | | | |
| 48 | 18 | | 1 | | | | | | |
| 48 | 20 | | 1 | | | | | | |
| 52 Cont. | | | 4 | | | | | X X | |
| 53 | | 20 | 1 | X | | | | X | |
| 53 | | 30 | 1 | | X | | | | |
| 53 | | 45 | 2 | | | | | X X | |
| 54 | 1 | 30 | 2 | X | X | X | | X | |
| 55 | 1 | 15 | 1 | X X X | | | | X | |
| 55 | 1 | 25 | 2 | | | | | | |
| 55 | 2 | 35 | 3 | | | X | | | |
| 55 | | 5 | 1 | | | | | | |
| 55 | | 10 | 1 | | | | | X X | |
| 55 | | 15 | 1 | | | | | | |
| 55 | | 20 | 1 | | | | | | |
| 55 | | 25 | 1 | | | | | | |
| 55 | | 30 | 3 | | | | | | |
| 56 | | 10 | 1 | | | X | | X X | |
| 56 | | 15 | 1 | | | | | | |
| 56 | | 20 | 1 | | | | | X X | |

SYSTEMS AND METHODS FOR REGULATING TEMPERATURE AND ILLUMINATION INTENSITY AT THE DISTAL TIP OF AN ENDOSCOPE

CROSS-REFERENCE

The present application relies on U.S. Patent Provisional Application No. 62/156,418, entitled "System and Method for Measurement of Temperature at the Distal Tip of an Endoscope", and filed on May 4, 2015, for priority. The present application also relies on U.S. Patent Provisional Application No. 62/235,768, entitled "A Method of Regulating Illumination for Multiple Viewing Element Endoscopes", and filed on Oct. 1, 2015, for priority. Both of the above-mentioned applications are herein incorporated by reference in their entirety.

The present application is also continuation-in-part of U.S. patent application Ser. No. 14/274,323 (the '323 application) entitled "An Endoscope Tip Position Visual Indicator and Heat Management System", and filed on May 9, 2014, which, in turn, relies on U.S. Patent Provisional Application No. 61/822,805, filed on May 13, 2013.

The '323 application is a continuation-in-part application of U.S. patent application Ser. No. 13/984,028, entitled "Multi-Element Cover for a Multi-Camera Endoscope", filed on Aug. 22, 2013 and issued as U.S. Pat. No. 9,101,266 on Aug. 11, 2015, which is a 371 National Stage Entry of PCT Application Number PCT/IL2012/050037, of the same title and filed on Feb. 6, 2012, which, in turn, relies upon U.S. Provisional Patent Application No. 61/439,948, filed on Feb. 7, 2011, for priority, and is herein incorporated by reference.

The '323 application is also a continuation-in-part application of U.S. patent application Ser. No. 13/992,021, entitled "Fluid Channeling Component of a Multi-Camera Endoscope", filed on Jun. 6, 2013 and issued as U.S. Pat. No. 9,320,419 on Apr. 26, 2016, which is a 371 National Stage Entry of PCT Application Number PCT/IL2011/050050, entitled "Flexible Electronic Circuit Board Multi-Camera Endoscope" and filed on Dec. 8, 2011, which, in turn, relies upon U.S. Provisional Patent Application No. 61/421,240, filed on Dec. 9, 2010, for priority, and is herein incorporated by reference.

The '323 application is also a continuation-in-part application of U.S. patent application Ser. No. 13/992,014, entitled "Flexible Electronic Circuit Board for a Multi-Camera Endoscope" and filed on Jun. 6, 2013, which is a 371 National Stage Entry of PCT Application Number PCT/IL2011/050049, of the same title and filed on Dec. 8, 2011, which, in turn, relies upon U.S. Provisional Patent Application No. 61/421,238, filed on Dec. 9, 2010, for priority, and is herein incorporated by reference.

The '323 application is also a continuation-in-part application of U.S. patent application Ser. No. 13/882,004, entitled "Optical Systems for Multi-Sensor Endoscopes" and filed on May 23, 2013, which is a 371 National Stage Entry of PCT Application Number PCT/IL2011/000832, of the same title and filed on Oct. 27, 2011, which, in turn, relies upon U.S. Provisional Patent Application No. 61/407,495, filed on Oct. 28, 2010, for priority, and is herein incorporated by reference.

The '323 application is also a continuation-in-part application of U.S. patent application Ser. No. 13/822,908, entitled "Multi-Camera Endoscope Having Fluid Channels" and filed on Mar. 13, 2013, which is a 371 National Stage Entry of PCT Application Number PCT/IL2011/000745, of the same title and filed on Sep. 20, 2011, which, in turn, relies upon U.S. Provisional Patent Application No. 61/384,354, filed on Sep. 20, 2010, for priority, and is herein incorporated by reference.

The '323 application is a continuation-in-part application of U.S. patent application Ser. No. 13/713,449, entitled "Removable Tip Endoscope" and filed on Dec. 13, 2012, which, in turn, relies upon U.S. Provisional Patent Application No. 61/569,796, of the same title and filed on Dec. 13, 2011, for priority, and is herein incorporated by reference.

The '323 application is also a continuation-in-part application of the following United States Patent Applications, which are herein incorporated by reference in their entirety:

U.S. patent application Ser. No. 13/655,120, entitled "Multi-Camera Endoscope" and filed on Oct. 18, 2012;

U.S. patent application Ser. No. 13/212,627, entitled "Multi-Viewing Element Endoscope" and filed on Aug. 18, 2011; and U.S. patent application Ser. No. 13/190,968, entitled "Multi-Camera Endoscope", filed on Jul. 26, 2011 and issued as U.S. Pat. No. 9,101,268 on Aug. 11, 2015, all of which are continuation-in-part applications of U.S. patent application Ser. No. 13/119,032, entitled "Multi-Camera Endoscope" and filed on Jul. 15, 2011, which is a 371 National Stage Entry of PCT Application Number PCT/IL2010/000476, of the same title and filed on Jun. 16, 2010, which, in turn, relies upon U.S. Provisional Patent Application No. 61/218,085 filed on Jun. 18, 2009, for priority.

The '323 application is also a continuation-in-part application of U.S. patent application Ser. No. 13/413,252, entitled "Multi Camera Endoscope Assembly Having Multiple Working Channels", filed on Mar. 6, 2012 and issued as U.S. Pat. No. 9,101,287 on Aug. 11, 2015, which, in turn, relies upon U.S. Provisional Patent Application No. 61/449,746, of the same title and filed on Mar. 7, 2011, for priority, and is herein incorporated by reference.

The '323 application is also a continuation-in-part application of U.S. patent application Ser. No. 13/413,141, entitled "Multi Camera Endoscope Having a Side Service Channel", filed on Mar.6, 2012, and issued as U.S. Pat. No. 8,926,502 on Jan. 6, 2015, which, in turn, relies upon U.S. Provisional Patent Application No. 61/449,743, of the same title and filed on Mar. 7, 2011, for priority, and is herein incorporated by reference.

The '323 application is also a continuation-in-part application of U.S. patent application Ser. No. 13/413,059, entitled "Endoscope Circuit Board Assembly" and filed on Mar. 6, 2012, which, in turn, relies upon U.S. Provisional Patent Application No. 61/449,741, of the same title and filed on Mar. 7, 2011, for priority, and is herein incorporated by reference.

The '323 application is also a continuation-in-part application of U.S. patent application Ser. No. 13/412,974, entitled "Camera Assembly for Medical Probes" and filed on Mar. 6, 2012, which, in turn, relies upon U.S. Provisional Patent Application No. 61/449,739, of the same title and filed on Mar. 7, 2011, for priority, and is herein incorporated by reference.

The present application relates to U.S. patent application Ser. No. 14/705,355, entitled "Systems and Methods of Distributing Illumination for Multiple Viewing Element and Multiple Illuminator Endoscopes" and filed on May 6, 2015, which relies on, for priority, U.S. Provisional Patent Application No. 61/989,895, entitled "Multi-Illuminator Endoscopic Lens Actuation Systems" and filed on May 7, 2014, which is herein incorporated by reference in its entirety.

The present application relates to U.S. patent application Ser. No. 14/603,137, entitled "Image Capture and Video Processing Systems and Methods for Multiple Viewing Element Endoscopes", filed on Jan. 22, 2015, which relies on U.S. Provisional Patent Application No. 61/930,101, entitled "Daisy Chain Multi-Sensor Endoscopic System" and filed on Jan. 22, 2014 and U.S. Provisional Patent Application No. 61/948,012, entitled "Parallel Illuminating Systems" and filed on Mar. 4, 2014.

All of the above-mentioned applications are herein incorporated by reference in their entirety.

FIELD

The present specification relates generally to endoscopes with multiple viewing elements, and more specifically, to systems and methods for regulating the temperature at the distal tip of an endoscope and for regulating the illumination level of an endoscope based on an activity level.

BACKGROUND

Endoscopes have attained great acceptance within the medical community since they provide a means for performing procedures with minimal patient trauma while enabling the physician to view the internal anatomy of the patient. Over the years, numerous endoscopes have been developed and categorized according to specific applications, such as, cystoscopy, colonoscopy, laparoscopy, and upper gastrointestinal endoscopy, among others. Endoscopes may be inserted into the body's natural orifices or through an incision in the skin.

An endoscope typically comprises an elongated tubular shaft, rigid or flexible, having a video camera or a fiber optic lens assembly at its distal end. The shaft is connected to a handle which sometimes includes an ocular for direct viewing. Viewing is also usually possible via an external screen. Various surgical tools may be inserted through a working channel in the endoscope for performing different surgical procedures.

Endoscopes, such as colonoscopes and gastroscopes, that are currently being used, typically have at least a front camera for viewing an internal organ, such as, the colon, an illuminator for illuminating the field of view of the camera, a fluid injector for cleaning the camera lens, and a working channel for insertion of surgical tools, for example, tools for removing polyps found in the colon. Commonly used illuminators comprise optical fibers which transmit light, generated remotely, to the endoscope tip section. In more currently developed endoscopes, discrete illuminators such as light-emitting diodes (LEDs) have been incorporated for providing illumination.

Multiple viewing elements endoscopes comprise two or more sets of optical assemblies, each having an optical lens associated with an image sensor and two or more illuminators. Other than flexible electronic boards, separate circuit boards are employed to hold and support the illuminators in a desired position with reference to the associated optical assemblies. The use of additional circuit boards increases the number of components that are required to be fitted into the limited space available in the tip of the endoscope. Since most of the components dissipate some power in the form of heat, use of multiple sets of illuminators, sensors and viewing elements produces a significant amount of heat in the distal tip during an endoscopic procedure. Tip heating not only causes discomfort to the patient, but may also affect performance of some of the electronic components inside the tip. Failure of a component to operate due to too high a temperature is also known. In some cases, the failure is reversible and vanishes as temperature drops again to normal levels, while in others it is irreversible. In particular, under high temperature conditions, LEDs exhibit reduced brightness and a shift in chromaticity towards blue. In general, imagers experience higher noise and a change in image characteristics such as hue, saturation, brightness and contrast at higher temperatures. Hence, there is a need for a method and system to measure and regulate the temperature of the distal tip. Existing methods of measuring the temperature at the distal tip involve the use of a dedicated sensor and wiring, which occupy valuable space and add to the crowding of components inside the tip.

Therefore, there is a need for methods and devices for measuring the temperature of a distal tip which can advantageously use existing components located within the tip of a multiple viewing elements endoscope. Such a method should provide for dynamic measurement of temperature, so that the temperature may be adjusted by reducing the power of suitable components, thus avoiding overheating.

Conventional multiple viewing elements endoscopes typically comprise multiple sets of illuminators that are operated in a very sub-optimal manner. A multiple sensor or multiple viewing elements endoscope tip section comprising a front-pointing camera and two or more side-pointing cameras positioned at or in proximity to a distal end of the tip section and a working channel configured for insertion of a surgical tool is disclosed in U.S. patent application Ser. No. 13/655,120, entitled "Multi-Camera Endoscope" and filed on Oct. 18, 2012, assigned to the Applicant of the present specification and herein incorporated by reference in its entirety. As described in the '120 application, the field of view (FOV) of each camera sensor in a multiple sensor endoscope is illuminated by two or more illuminators that are light emitting diodes (LEDs). Thus, multiple sensor endoscopes' tips that include a right pointing camera or viewing element, a front pointing camera or viewing element and a left pointing camera or viewing element may include a minimum of six or more LEDs. In some embodiments, each viewing element comprises three illuminators, totaling nine LEDs. Similarly, multiple sensor endoscope tip sections that include a front pointing camera or viewing element and a side pointing camera or viewing element may include four, five or more LEDs.

Since the depth corresponding to the field of view of a camera can vary significantly depending on the orientation of distal tip during a colonoscopy procedure (for example, when navigated through a patient's colon), illuminating all LEDs with a fixed illumination intensity is sub-optimal. Fixed illumination intensity may prove to be too weak in some orientations for example and may drive the camera sensor arrays beyond their dazzle limits due to light reflection from a nearby wall in other orientations. In some cases, when driven beyond their dazzle limits, camera sensor arrays such as Charge-Coupled Devices (CCDs) may create saturation and blooming that may appear as a white streak or blob in the generated images.

Further, keeping all LEDs illuminated at a constant intensity for long periods of time may result in production of excessive heat at the tip section of the endoscope. High temperature may adversely affect tissues during an endoscopic procedure. FIG. 1 shows a table 100 illustrating a quantitative relationship between temperature and thermal impact on porcine skin as published in "Studies of Thermal Injury: II. The Relative Importance of Time and Surface Temperature in the Causation of Cutaneous Burns", *The*

*American Journal of Pathology* 23.5 (1947): 695 by Moritz, A. Re, and F. C. Henriques Jr. The table 100 provides sub-threshold exposures 105 as well as threshold and supra-threshold exposures 110 related to an increasing temperature 115 and time of exposure 120. It is evident that severity of thermal injury to tissues increases with an increase in temperature and time of exposure.

One approach for controlling the illumination of a multiple illuminator endoscope system may be provided by dynamically controlling the emitted light or luminance intensities. It is further desirable to regulate the illumination of the multiple illuminators automatically in response to the usage of the endoscope tip section.

Therefore, there is a need for systems and methods for automatically detecting the activity level corresponding to the tip section of an endoscope and responsively regulating the luminance intensity level of each illuminator associated with the tip section.

As such, it would also be highly advantageous to provide a method of automatically detecting if the endoscope tip section is stationary or in motion and responsively regulating the luminance intensity level of each illuminator independently.

SUMMARY

In some embodiments, the present specification discloses an endoscopy system capable of measuring and regulating the temperature of its distal tip comprising: a plurality of viewing elements located in the endoscope tip, wherein each of said viewing elements comprises an image sensor and a lens assembly and is associated with one or more light emitting diode (LED) illuminators; a circuit board comprising a circuit for measuring a voltage across each of said LED illuminators; and a controller programmed to compute a temperature of each of said LED illuminators by using said measured voltage and a function representing a relationship between LED voltage and LED junction temperature for a given current.

Optionally, the controller is further programmed to compute an average of LED junction temperatures and use that average to compute the temperature at a given point on the distal tip.

Optionally, the controller is further programmed to reduce a power of the LED illuminators if the average LED junction temperature exceeds a pre-determined limit.

Optionally, the function representing the relationship between LED voltage and LED junction temperature is pre-determined by measuring LED voltage and LED junction temperature for a range of LED currents and identifying a relationship between LED voltage and junction temperature.

Optionally, said function is separately estimated for each LED illuminator present in each illuminator during an evaluation phase of said endoscopy system. Still optionally, said function is estimated using regression analysis.

Optionally, a relationship between the average of LED junction temperatures and the temperature at a given point on the distal tip is pre-determined by measuring an average LED junction temperature and a corresponding temperature at a given point on the distal tip for a range of LED currents and identifying a relationship between average LED junction temperatures and temperatures for the given point on the distal tip. Still optionally, said relationship is estimated using regression analysis.

In some embodiments, the present specification discloses a method for determining a temperature in an endoscope, without using a separate, dedicated temperature sensor, wherein said endoscope comprises a plurality of viewing elements located in a distal tip of the endoscope and wherein each of said viewing elements comprises an image sensor and a lens assembly and is associated with one or more LED illuminators, said method comprising: measuring a voltage across at least one of said LED illuminators; and computing a junction temperature for the at least one of said LED illuminators by using a value of the measured voltage and a function representing a relationship between LED voltage and LED junction temperature for a given current and for the at least one of said LED illuminators.

Optionally, said method further comprises the step of computing an average of junction temperatures of at least two LED illuminators present in the system and using that average to compute the temperature at a given point on the distal tip.

Optionally, an average of junction temperatures of all the LED illuminators is used to estimate the temperature at a given point on the distal tip. Still optionally, an average of junction temperature of only the LED illuminators which are directly adjacent a given point on the distal tip are used to estimate the temperature at said given point.

Optionally, a power of the at least one of said LED illuminator is reduced if a junction temperature of said LED illuminator exceeds a pre-determined limit.

Optionally, the function representing the relationship between LED voltage and LED junction temperature is pre-determined by measuring LED voltage and LED junction temperature for a range of LED currents and identifying a relationship between the LED voltage and LED junction temperature.

Optionally, a relationship between average LED junction temperature and the temperature at a given point on the distal tip is pre-determined by measuring average LED junction temperature and the temperature at a given point on the distal tip for a range of LED currents and identifying a relationship between the average LED junction temperature and the temperature at the given point.

In some embodiments, the present specification discloses a method of regulating a luminance intensity of one or more illuminators of an endoscope tip section having a plurality of viewing elements, wherein each of the plurality of viewing elements is associated with at least one of said one or more illuminators, the method comprising: obtaining a first sample of images from each of the plurality of viewing elements at a first time instance, wherein each image of the first sample is divided into a plurality of blocks; obtaining a second sample of images from each of the plurality of viewing elements at a second time instance, wherein each image of the second sample is divided into a plurality of blocks; calculating an average luminance for each block of the first sample and for each block of the second sample; for each block, computing a change in the average luminance between the first sample and second sample; identifying blocks having a maximum average luminance change among images of the first sample and the second sample; calculating a fraction of a total number of blocks whose maximum average luminance change exceeds a first threshold value; and depending upon whether said fraction of to the total number blocks does or does not exceed a second threshold value, performing one of the following steps: changing the luminance intensity of the at least one of said one or more illuminators from a first intensity level to a second intensity level; changing the luminance intensity of the at least one of said one or more illuminators from the second intensity level to the first intensity level; or, maintaining a luminance intensity of the at least one of said one or more illuminators at the first intensity level or the second intensity level.

Optionally, said first intensity level is higher than the second intensity level.

Optionally, if said fraction of the total number of blocks exceed the second threshold value and the luminance intensity of the at least one of said one or more illuminators is at a second intensity level, said luminance intensity is changed from said second intensity level to said first intensity level.

Optionally, if said fraction of the total number of blocks is lower than said second threshold value and the luminance intensity of the at least one of said one or more illuminators is at a first intensity level, said luminance intensity is changed from said first intensity level to said second intensity level.

Optionally, said first intensity level ranges from 20 mA to 100 mA.

Optionally, said first intensity level corresponds to an active state of the at least one of said one or more illuminators.

Optionally, the change of the luminance intensity of the at least one of said one or more illuminators to the first intensity level is indicative of a motion of the distal tip section relative to its surroundings.

Optionally, the change of the luminance intensity of the at least one of said one or more illuminators to the first intensity level is indicative of at least one external object being brought within a predefined distance from the distal tip section. Optionally, the predefined distance is less than or equal to 5 centimeters from the distal tip section.

Optionally, the second intensity level corresponds to a passive state of the at least one of said one or more illuminators.

Optionally, the change of the luminance intensity of the at least one of said one or more illuminators from the first intensity level to the second intensity level is indicative of the distal tip section being stationary relative to its surroundings.

Optionally, said first and second time instances differ by 0.5 seconds.

Optionally, said first and second thresholds are derived by computing a luminance histogram for the first sample and the second sample.

In some embodiments, the present specification discloses an endoscope tip section having a plurality of viewing elements and a processor, wherein each of the plurality of viewing elements has one or more illuminators associated therewith and the processor is configured to regulate luminance intensity of at least one illuminator by: obtaining a first sample of images from each of the plurality of viewing elements at a first time instance, wherein each image of the first sample is divided into a plurality of blocks; obtaining a second sample of images from each of the plurality of viewing elements at a second time instance, wherein each image of the second sample is divided into a plurality of blocks; calculating an average luminance for each block of the first and second sample of images; for each block, computing an absolute value of average luminance change between the first and second sample of images; identifying blocks having maximum absolute average luminance change among images corresponding to the plurality of viewing elements; calculating a fraction of the total number of blocks whose maximum average luminance change exceeds a first threshold value; and depending upon whether said fraction of blocks does or does not exceed a second threshold value performing one of the following steps: changing the luminance intensity of said at least one illuminator from a first intensity level to a second intensity level; changing the luminance intensity of said at least one illuminator from a second intensity level to a first intensity level; or, maintaining the luminance intensity of said at least one illuminator at the first or second intensity level.

In some embodiments, the present specification discloses an endoscope tip section having a plurality of viewing elements and a processor, wherein each of the plurality of viewing elements has one or more illuminators associated therewith and the processor is configured to regulate luminance intensity of at least one illuminator by detecting whether said endoscope tip section is in an active state or a passive state.

Optionally, the process of detecting whether said endoscope tip section is in an active state or a passive state comprises: obtaining a first sample of images from each of the plurality of viewing elements at a first time instance, wherein each image of the first sample is divided into a plurality of blocks; obtaining a second sample of images from each of the plurality of viewing elements at a second time instance, wherein each image of the second sample is divided into a plurality of blocks; calculating an average luminance for each block of the first and second sample of images; for each block, computing an absolute value of average luminance change between the first and second sample of images; identifying blocks having maximum absolute average luminance change among images corresponding to the plurality of viewing elements; and, calculating a fraction of the total number of blocks whose maximum average luminance change exceeds a first threshold value.

Optionally, depending upon whether said fraction of total number of blocks does or does not exceed a second threshold value the process may include performing one of the following steps: changing the luminance intensity of said at least one illuminator from a first intensity level to a second intensity level; changing the luminance intensity of said at least one illuminator from a second intensity level to a first intensity level; or, maintaining the luminance intensity of said at least one illuminator at the first or second intensity level.

In some embodiments, the present specification discloses a method of regulating luminance intensity of at least one illuminator of an endoscope tip section having a plurality of viewing elements, wherein each of the plurality of viewing elements is with associated one or more illuminators, the method comprising: obtaining a first sample of images from each of the plurality of viewing elements at a first time instance, wherein each image of the first sample is divided into a plurality of blocks; obtaining a second sample of images from each of the plurality of viewing elements at a second time instance, wherein each image of the second sample is divided into a plurality of blocks; calculating an average luminance for each block of the first and second sample of images; for each block, computing an absolute value of average luminance change between the first and second sample of images; identifying blocks having maximum absolute average luminance change among images corresponding to the plurality of viewing elements; and, calculating a fraction of the total number of blocks whose maximum average luminance change exceeds a first threshold value.

Optionally, depending upon whether said fraction of the total number of blocks does or does not exceed a second value threshold the method may include performing one of the following steps: changing the luminance intensity of said at least one illuminator from a first intensity level to a second intensity level; changing the luminance intensity of said at least one illuminator from a second intensity level to a first intensity level; or, maintaining the luminance intensity of said at least one illuminator at the first or second intensity level.

The aforementioned and other embodiments of the present specification shall be described in greater depth in the drawings and detailed description provided below.

BRIEF DESCRIPTION OF THE DRAWINGS

These and other features and advantages of the present specification will be appreciated, as they become better understood by reference to the following detailed description when considered in connection with the accompanying drawings, wherein:

Figure 1:
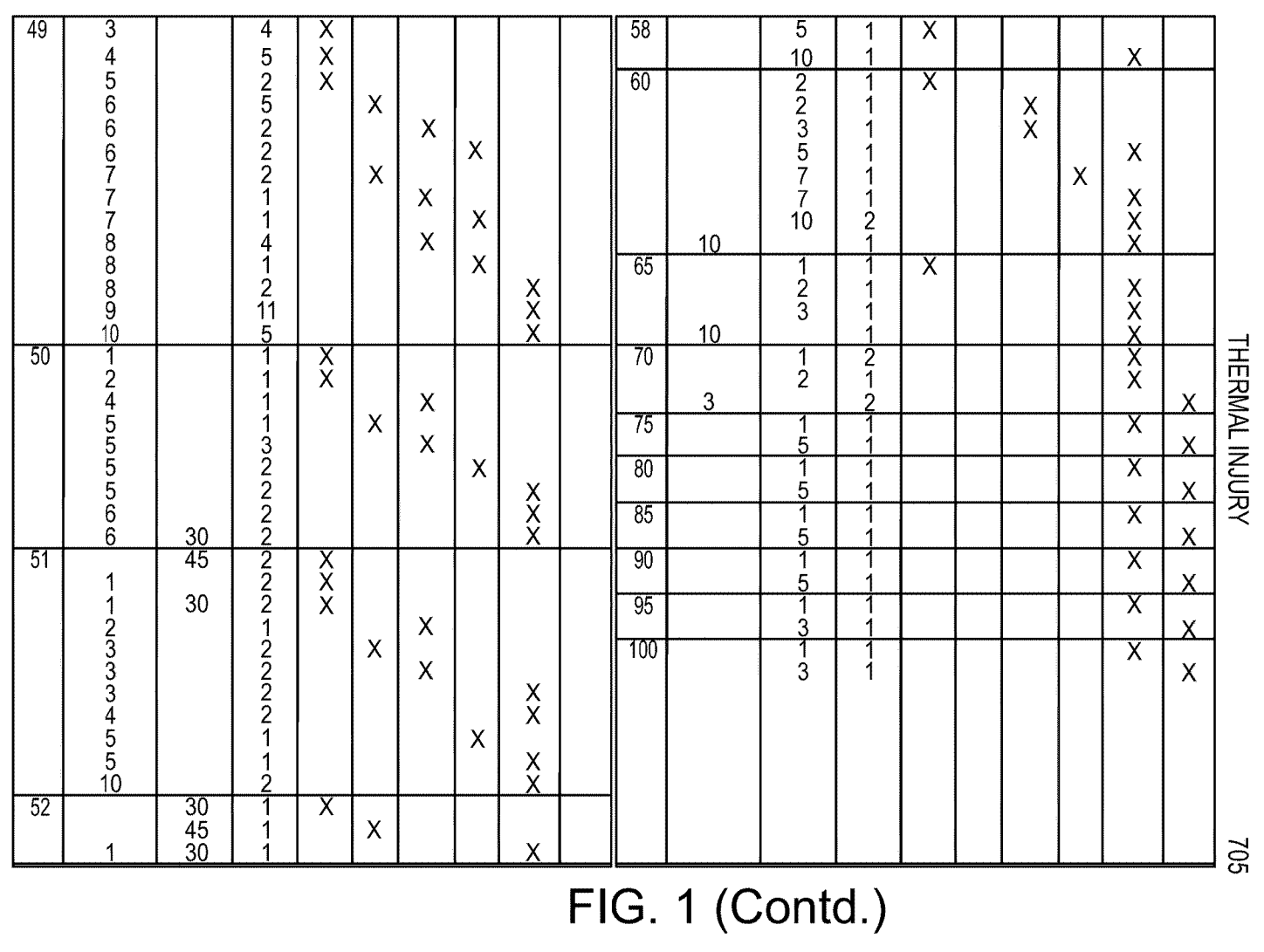

FIG. 1 is a table illustrating time-surface temperature thresholds for thermal injury of porcine skin;

DETAILED DESCRIPTION

Figure 2A:
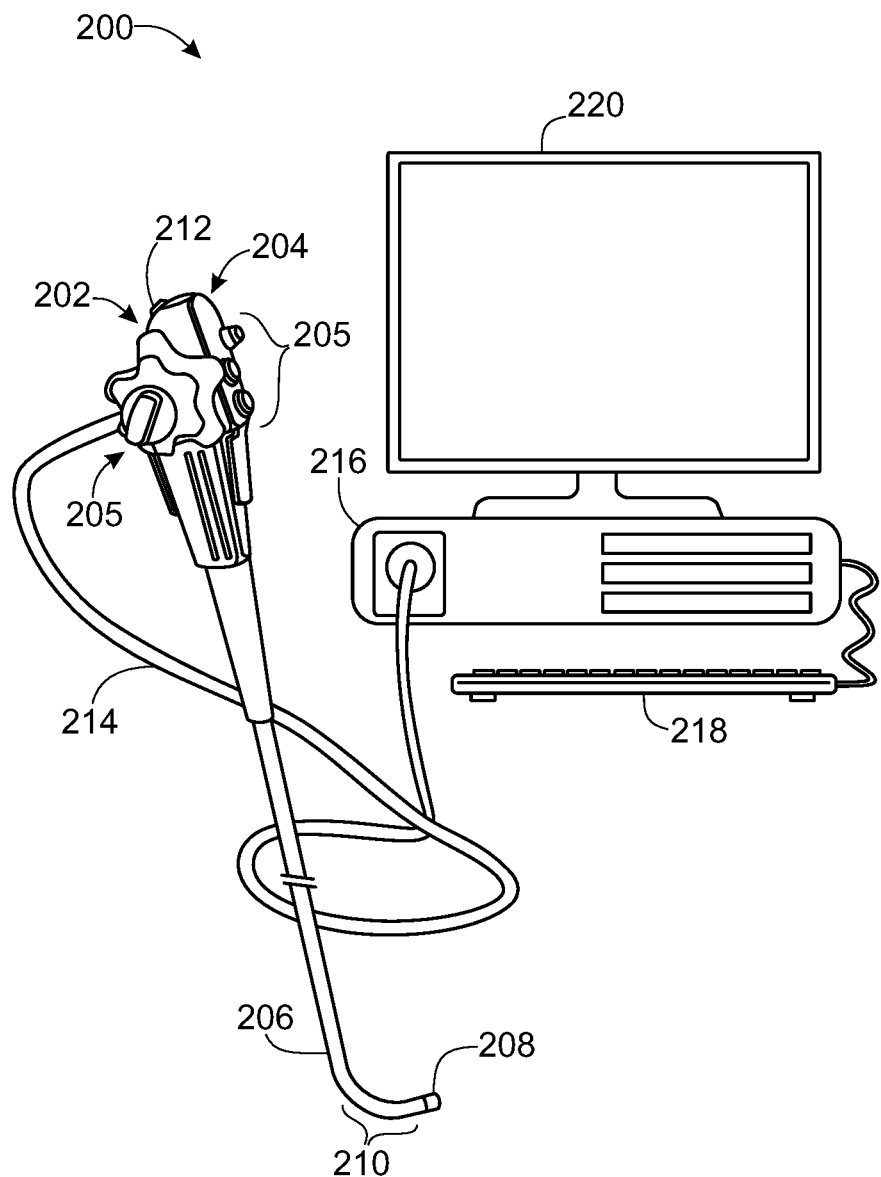
FIG. 2A illustrates an exemplary multiple viewing elements endoscopy system, as used in an embodiment of the present specification.

In embodiments, the present specification discloses systems and methods for regulating the temperature at the distal tip of an endoscope and systems and methods for regulating the illumination intensity of an endoscope based on an activity level. Individually or discretely regulating the illumination intensity of each illuminator reduces the overall power consumption of the endoscope and thus reduces heat production in the endoscope's tip section.

In an embodiment, the present specification discloses a system and method for measuring and regulating the temperature at the distal tip of an endoscope. In some embodiments, the present specification discloses a system and method for determining the temperature of the tip of a multiple viewing elements endoscope, without making use of a dedicated temperature sensor and/or associated circuitry which would occupy additional space in the tip section. In an embodiment, temperature determination is based upon measurement of at least one junction temperature of LED illuminators positioned within the tip section. Optionally, the temperature measurement is used for taking corrective actions if the temperature reading and/or calculation does not fall within a pre-determined range, such as if the temperature exceeds a pre-determined threshold limit. Optionally, a temperature measurement is used for optimizing image sensor parameters, since the performance of image sensors is affected by changes in ambient temperature.

In accordance with an embodiment, the present specification also discloses a system and method for regulating the illumination intensity of each illuminator independently in a multiple viewing elements endoscope. In embodiments of the present specification, the system dynamically controls the illumination intensity of specific illuminator devices and ensures that each device is operated in the most optimal manner depending on the activity level and orientation of the distal tip.

In conventional endoscopes, fixed illumination intensity may prove to be weak in certain directions and may drive the camera sensor arrays beyond their dazzle limits due to light reflection from a nearby wall in other directions. In such circumstances, if the illumination intensity of all the illuminator devices is increased or decreased together, it may solve the problem in one direction but may further aggravate the problem in other directions. For example, reducing the illumination intensity may prevent dazzle in the direction in which the intensity was high but it may deteriorate the image quality in the direction in which the illumination intensity was already weak.

Another advantage of regulating each illuminator's illumination intensity independently is that the different types of illuminators may be switched between on and off states on demand or, in the alternative, may be set at a first intensity level, second intensity level and/or nth intensity level. For example, in an embodiment, the illuminators are specific blue and green wavelength range LEDs implementing a narrow band imaging technique, wherein the light of the specific blue and green wavelengths is used to enhance the detail of certain aspects of the surface of a mucosa, when needed.

In an embodiment, a processor of a main control unit, associated with the multiple viewing elements endoscope, is configured to vary the illumination intensity of each illuminator automatically using an image processing software program code.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

It should be noted herein that any feature or component described in association with a specific embodiment may be used and implemented with any other embodiment unless clearly indicated otherwise.

It is noted that the term "endoscope" as mentioned herein may refer particularly to a colonoscope and a gastroscope, according to some embodiments, but is not limited only to colonoscopies and/or gastroscopies. The term "endoscope" may refer to any instrument used to examine the interior of a hollow organ or cavity of the body.

Further, the systems and methods of the present specification may be implemented with any endoscope. An exemplary system is described in co-pending U.S. patent application Ser. No. 14/469,481, entitled "Circuit Board Assembly of A Multiple Viewing Elements Endoscope", filed on Aug. 26, 2014 and herein incorporated by reference in its entirety.

Reference is now made to FIG. 2A, which shows a multi-viewing elements endoscopy system 200. System 200 may include a multi-viewing elements endoscope 202. Multi-viewing elements endoscope 202 may include a handle 204, from which an elongated shaft 206 emerges. Elongated shaft 206 terminates with a tip section 208 which is turnable by way of a bending section 210. Handle 204 may be used for maneuvering elongated shaft 206 within a body cavity. The handle may include one or more buttons and/or knobs and/or switches 205 which control bending section 210 as well as functions such as fluid injection and suction. Handle 204 may further include at least one, and in some embodiments, one or more working channel openings 212 through which surgical tools may be inserted. In embodiments, the handle 204 also includes one and more side service/working channel openings.

Tip 208 may include multi-viewing elements. In accordance with an embodiment, tip 208 includes a front viewing element and one or more side viewing elements. In another embodiment, tip 208 may include only a front viewing element.

In addition, tip 208 may include one or more service/working channel exit point. In accordance with an embodiment, tip 208 includes a front service/working channel exit point and at least one side service channel exit point. In another embodiment, tip 208 may include two front service/working channel exit points.

A utility cable 214, also referred to as an umbilical tube, may connect between handle 204 and a Main Control Unit (MCU) 216. Utility cable 214 may include therein one or more fluid channels and one or more electrical channels. The electrical channel(s) may include at least one data cable for receiving video signals from the front and side-pointing viewing elements, as well as at least one power cable for providing electrical power to the viewing elements and to the discrete illuminators.

The main control unit 216 contains the controls required for displaying the images of internal organs captured by the endoscope 202. The main control unit 216 may govern power transmission to the endoscope's 202 tip section 208, such as for the tip section's viewing elements and illuminators. The main control unit 216 may further control one or more fluid, liquid and/or suction pump(s) which supply corresponding functionalities to the endoscope 202.

One or more input devices 218, such as a keyboard, a touch screen and the like may be connected to the main control unit 216 for the purpose of human interaction with the main control unit 216.

In the embodiment shown in FIG. 2A, the main control unit 216 comprises a screen/display 220 for displaying operation information concerning an endoscopy procedure when the endoscope 202 is in use. The screen 220 may be configured to display images and/or video streams received from the viewing elements of the multi-viewing element endoscope 202. The screen 220 may further be operative to display a user interface for allowing a human operator to set various features of the endoscopy system.

Optionally, the video streams received from the different viewing elements of the multi-viewing element endoscope 202 may be displayed separately on at least one monitor (not seen) by uploading information from the main control unit 216, either side-by-side or interchangeably (namely, the operator may switch between views from the different viewing elements manually). Alternatively, these video streams may be processed by the main control unit 216 to combine them into a single, panoramic video frame, based on an overlap between fields of view of the viewing elements. In an embodiment, two or more displays may be connected to the main control unit 216, each for displaying a video stream from a different viewing element of the multi-viewing element endoscope 202. The main control unit 216 is described in U.S. patent application Ser. No. 14/263,896, entitled "Video Processing in a Compact Multi-Viewing Element Endoscope System" and filed on Apr. 28, 2014, which is herein incorporated by reference in its entirety.

Figure 2B:
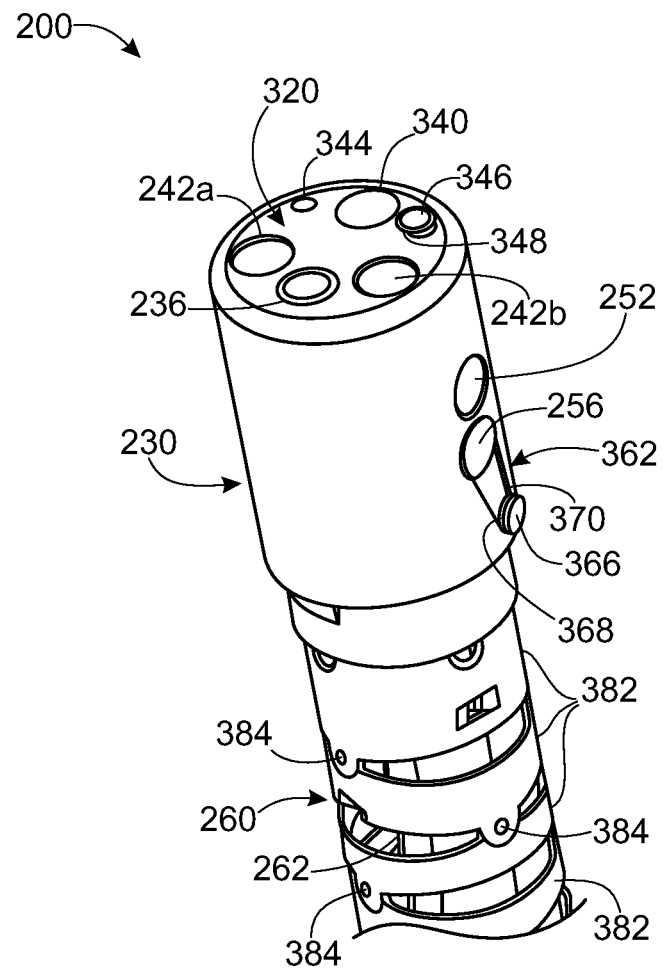
FIG. 2B illustrates an isometric, external view of an endoscope having multiple viewing elements in which the systems and methods described in the present specification may be implemented.

FIG. 2B is an isometric, external view of an endoscope having multiple viewing elements. Referring to FIG. 2B, tip or head 230 of endoscope 200 comprises at least a front pointing viewing element 236 and at least one side pointing viewing element 256. The viewing elements may be an image sensor, such as Charge Coupled Device (CCD) or a Complementary Metal Oxide Semiconductor (CMOS) imager. Further, the term "viewing element" may generally refer to an image sensor and the optical system/assembly related to the image sensor.

In an embodiment, the front viewing element 236 is located on the front face 320 of head 230. In an embodiment, the optical axis of the front viewing element is substantially directed along the long dimension of the endoscope. However, since the front viewing element typically has a wide angle, its Field of View (FOV) may include viewing directions at large angles relative to its optical axis. Additionally, optical windows 242a and 242b, which have discrete light sources such as Light Emitting Diodes (LEDs), are also seen on front face 320 of head 230. It should be noted that the number of LEDs used for illumination of the FOV may vary. Further, the LEDs used may be white light LEDs, infrared light LEDs, near infrared light LEDs, ultraviolet light LEDs or any other type of LED.

In an embodiment, distal opening 340 of working channel 262 is located on front face 320 of head 230, such that a surgical tool inserted through working channel 262 and deployed beyond front face 320 may be viewed by the front viewing element 236. Distal opening 344 of a fluid channel may preferably also be located on front face 320 of head 230. The fluid channel leading to distal opening 344 may be used as a jet channel for cleaning the colon.

Liquid injector 346 having a nozzle 348 aimed at front viewing element 236 is used for injecting fluid to wash contaminants such as blood, feces and other debris from front viewing element 236. Optionally, the same injector is used for cleaning both front viewing element 236 and one or both optical windows 242a and 242b. Injector 346 may receive fluid (for example, water and/or gas) from the fluid channel or may be fed by a dedicated cleaning fluid channel.

Visible on the side wall 362 of head 230 is the side pointing viewing element 256 and optical window 252 having a discrete light source such as LED. It may be noted that the number of the discrete light sources may vary. In one embodiment, optical axis of side pointing viewing element 256 may be substantially directed perpendicular to the long dimension of the endoscope. However, since side viewing element typically has a wide angle, its field of view may include viewing directions at large angles to its optical axis.

Liquid injector 366 having a nozzle 368 aimed at side viewing element 256 is used for injecting fluid to wash contaminants such as blood, feces and other debris from the side viewing element 256. Optionally, the same injector is used for cleaning both the side viewing element 256 and optical window 252. Preferably, injectors 346 and 366 are fed from same channel. An optional groove 370 helps direct the cleaning fluid from nozzle 368 towards side viewing element 256.

In the depicted embodiment, flexible shaft 260 is constructed of a plurality of links 382 connected to each other by pivots 384. Links 382 allows pushing, pulling and rotating the endoscope while pivots 384 provide limited flexibility. Not seen in this figure are the electrical cables supplying power to the LEDs.

It should be noted that while only one side pointing viewing element is seen in FIG. 2B, optionally, according to some embodiments, two or more side pointing viewing elements may be located within head 230. When two side pointing viewing elements are used, they are preferably installed such that their field of views are substantially opposing. According to some embodiments, different configurations and number of side pointing viewing elements are possible and covered within the general scope of the current specification.

Figure 2C:
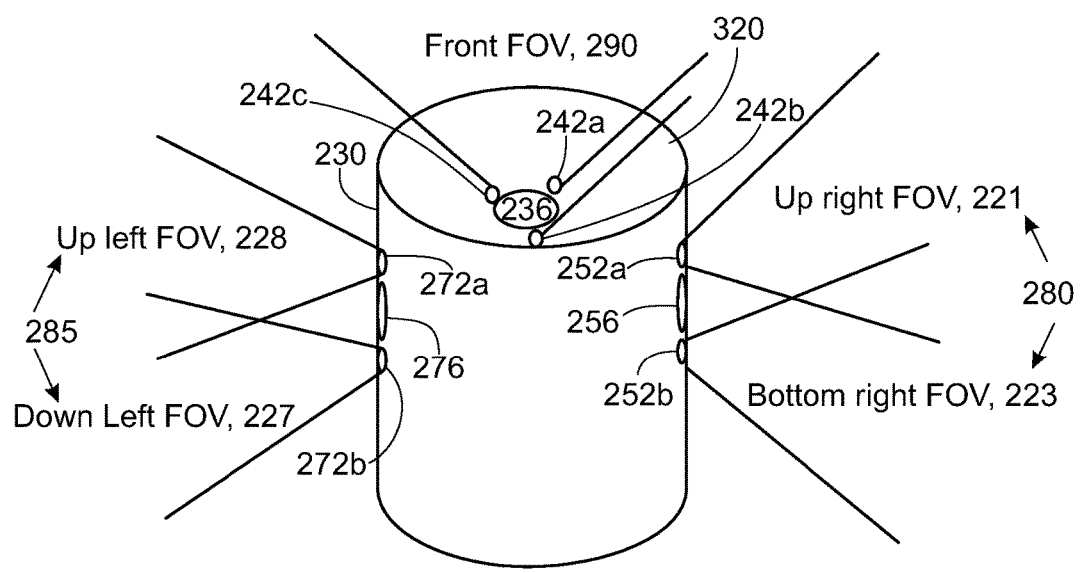
FIG. 2C illustrates an endoscope tip comprising multiple viewing elements and illuminators associated with such viewing elements in an endoscopy system in which the systems and methods described in the present specification may be implemented.

Reference is now made to FIG. 2C, which illustrates another embodiment of an exemplary multiple viewing elements endoscope tip section 230 comprising a plurality of viewing elements, also referred to as cameras or sensors, and an illuminating system comprising a plurality of illuminators wherein at least one illuminator is associated with each of the plurality of viewing elements, according to certain embodiments. The endoscope tip section 230 includes a front pointing viewing element 236, a first side pointing viewing element 256 and a second side pointing viewing element 276.

In accordance with an embodiment, the first side pointing viewing element 256 has two associated side pointing illuminators 252a and 252b illuminating an upper right field of view (FOV) 221 and a lower right FOV 223 (the FOVs 221 and 223 may partially overlap in various embodiments) to together illuminate a right FOV 280; the second side pointing viewing element 276 has two associated side pointing illuminators 272a and 272b, which respectively illuminate a lower left FOV portion 227 and an upper left FOV portion 228, together illuminating a left FOV 285; and the front pointing viewing element 236 has three associated front pointing illuminators 242a, 242b and 242c (the FOVs of the three front pointing illuminators may partially overlap in various embodiments), which together illuminate a front FOV 290. Persons of ordinary skill in the art should appreciate that the number of viewing elements and the number of illuminators associated with each of the viewing elements may vary in alternate embodiments. For example, an embodiment may comprise a front pointing viewing element and a side pointing viewing element wherein each of the front and side pointing viewing elements may have one, two or more illuminators associated with them. In accordance with various embodiments the viewing elements or cameras 236, 256 and 276 are associated with Charge-Coupled Device (CCD) or Complementary Metal Oxide Semiconductor (CMOS) image sensor arrays. Also, front illuminators 242a, 242b and 242c and side illuminators 252a, 252b, 272a, 272b are, in an embodiment, discrete illuminators and include a light-emitting diode (LED), which may be a white light LED, an infrared light LED, a near infrared light LED, an ultraviolet light LED or any other LED. In an embodiment, each illuminator includes one, two or more LED. In various embodiments, all the illuminators include the same type of one or more LEDs (white, infrared, near infrared, ultraviolet, etc.) or a combination of the different types of one or more LEDs. The term "discrete", concerning discrete illuminator, refers to an illumination source, which generates light locally and internally, in contrast to a non-discrete illuminator, which may be, for example, a fiber optic merely transmitting light generated remotely.

In accordance with an embodiment, each of the first side pointing illuminators 252a, 252b include a single LED that are serially connected to each other and each of the second side pointing illuminators 272a, 272b include a single LED that are also serially connected to each other. In one embodiment, each of the front pointing illuminators 242a, 242b, 242c includes a single LED and the three LEDs (corresponding to the illuminators 242a, 242b, and 242c) are connected serially to each other. In another embodiment, each of the front pointing illuminators 242a, 242b, 242c includes two LEDs (forming three pairs of LEDs) that are connected in parallel to each other within their corresponding illuminators 242a, 242b, 242c; however the three illuminators 242a, 242b, 242c (including the three pairs of LEDs)connect to each other serially.

It should be understood that the endoscope tip section 230 includes a working channel, a fluid injector channel, a jet channel having an opening positioned on the front face 320 that is configured to insert surgical tools and to inject fluids or gases, a flexible electronic circuit board configured to carry the front and side viewing elements along with the associated illuminators and objective lens systems, the wiring connections between these components and a cable connecting the endoscopic tip 230 to an endoscope handle which in turn is coupled to an external main control unit and a display.

Figure 3:
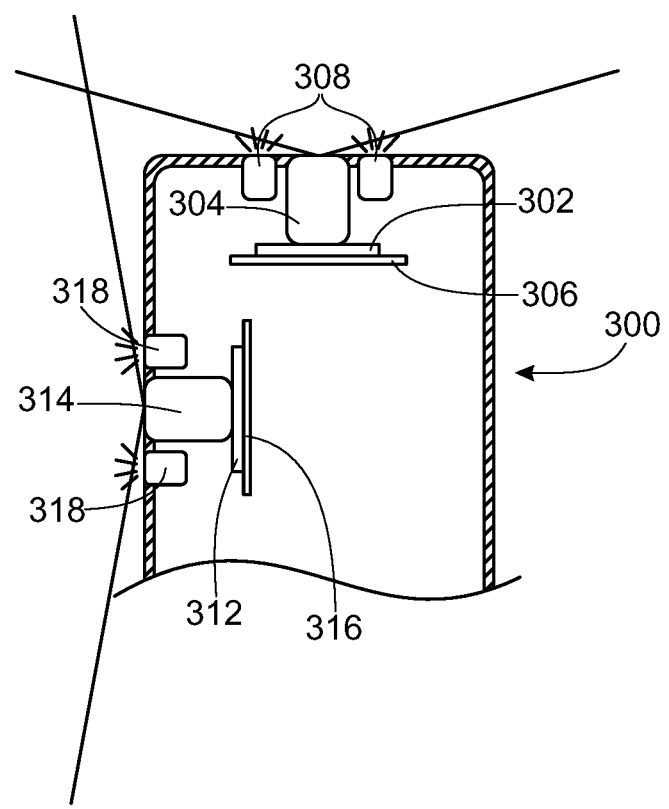
FIG. 3 illustrates a cross-sectional view of a tip section of a multi-camera endoscope, according to some embodiments.

Reference is now made to FIG. 3, which shows a cross-sectional view of a tip section 300 of a multiple viewing elements endoscope, according to an embodiment. In an embodiment, the tip section 300 includes a front-pointing image sensor 302, such as a Charge Coupled Device (CCD) or a Complementary Metal Oxide Semiconductor (CMOS) image sensor. In an embodiment, the front-pointing image sensor 302 is mounted on an integrated circuit board 306, which may be rigid or flexible in different embodiments. In an embodiment, the integrated circuit board 306 supplies front-pointing image sensor 302 with the necessary electrical power and derives still images and/or video feeds captured by the image sensor. In an embodiment, the integrated circuit board 306 is connected to a set of electrical cables (not shown) which in an embodiment are threaded through an electrical channel running through the elongated shaft of the endoscope. In embodiments, the front-pointing image sensor 302 is coupled to a lens assembly 304 which is mounted on top of it and provides the necessary optics for receiving images. In embodiments, the lens assembly 304 includes a plurality of lenses, static or movable, which may provide a field of view of at least 90 degrees and up to essentially 180 degrees. In an embodiment, lens assembly comprises fisheye lenses. Front-pointing image sensor 302 and lens assembly 304, with or without integrated circuit board 306, may be jointly referred to as a "front pointing viewing element".

In embodiments, one or more discrete front illuminators 308, such as LEDs, are placed next to lens assembly 304, for illuminating its field of view. Optionally, discrete front illuminators 308 are attached to the same integrated circuit board 306 on which front-pointing image sensor 302 is mounted (this configuration is not shown).

In an embodiment, the tip section 300 further includes a side-pointing image sensor 312, such as a Charge Coupled Device (CCD) or a Complementary Metal Oxide Semiconductor (CMOS) image sensor. In an embodiment, the side-pointing image sensor 312 is mounted on an integrated circuit board 316, which may be rigid or flexible in different embodiments. In an embodiment, the integrated circuit board 316 supplies side-pointing image sensor 312 with the necessary electrical power and derives still images and/or video feeds captured by the image sensor. In an embodiment, the side-pointing image sensor 312 is coupled to a lens assembly 314 which is mounted on top of it and provides the necessary optics for receiving images. Side-pointing image sensor 312 and lens assembly 314, with or without integrated circuit board 316, may be jointly referred to as a "side pointing viewing element".

In embodiments, one or more discrete side illuminators 318, such as LEDs, are placed next to lens assembly 314, for illuminating its field of view. Optionally, discrete front illuminators 318 are attached to the same integrated circuit board 316 on which side-pointing image sensor 312 is mounted (this configuration is not shown).

In another configuration, integrated circuit boards 306 and 316 comprise a single integrated circuit board on which both front and side-pointing image sensors 302 and 312 are mounted. In embodiments, the front and side-pointing image sensors 302 and 312 may be similar or identical in terms of, for example, field of view, resolution, light sensitivity, pixel size, focal length, focal distance and/or the like. Further, there may be two side-pointing image sensors, as described above.

One of ordinary skill in the art would appreciate that having multiple cameras and LED-based illuminants in the tip increases heat dissipation. During an endoscopy procedure, the distal tip's temperature is usually moderated by the heat dissipating properties of the patient, the gas flow, and the water jets. However, it is desirable to provide a dynamic regulation of temperature in the distal tip in order to lower the stress on the electronic components, thereby improving both performance and mean time between failures (MTBF). A device with a higher MTBF has higher reliability. Further, an increase in the number of components necessarily implies that more components are required to be tested in BIT (Built-In Test). Conventional systems cannot identify LED malfunctions and failures in the distal tip, such as short or open circuits or unassembled LEDs since LED voltages are not measured.

The present specification achieves the dual purpose of temperature measurement and functional testing at the distal tip by using the voltage-current dependency of the illuminators (LEDs) themselves. The methods of the present specification takes advantage of the premise that for any given current (forward current, If), an LED's voltage (forward voltage, Vf) drops as its junction temperature rises. This behavior applies to all LEDs at any forward current. Hence, an LED can be used as a temperature sensor once its forward current is known. The present methods therefore, enable measurement of temperature at the distal tip without using dedicated temperature sensors and wiring. This conserves valuable space in the distal tip and also provides a means for immediate detection of any LED malfunction in the tip.

Figure 4:
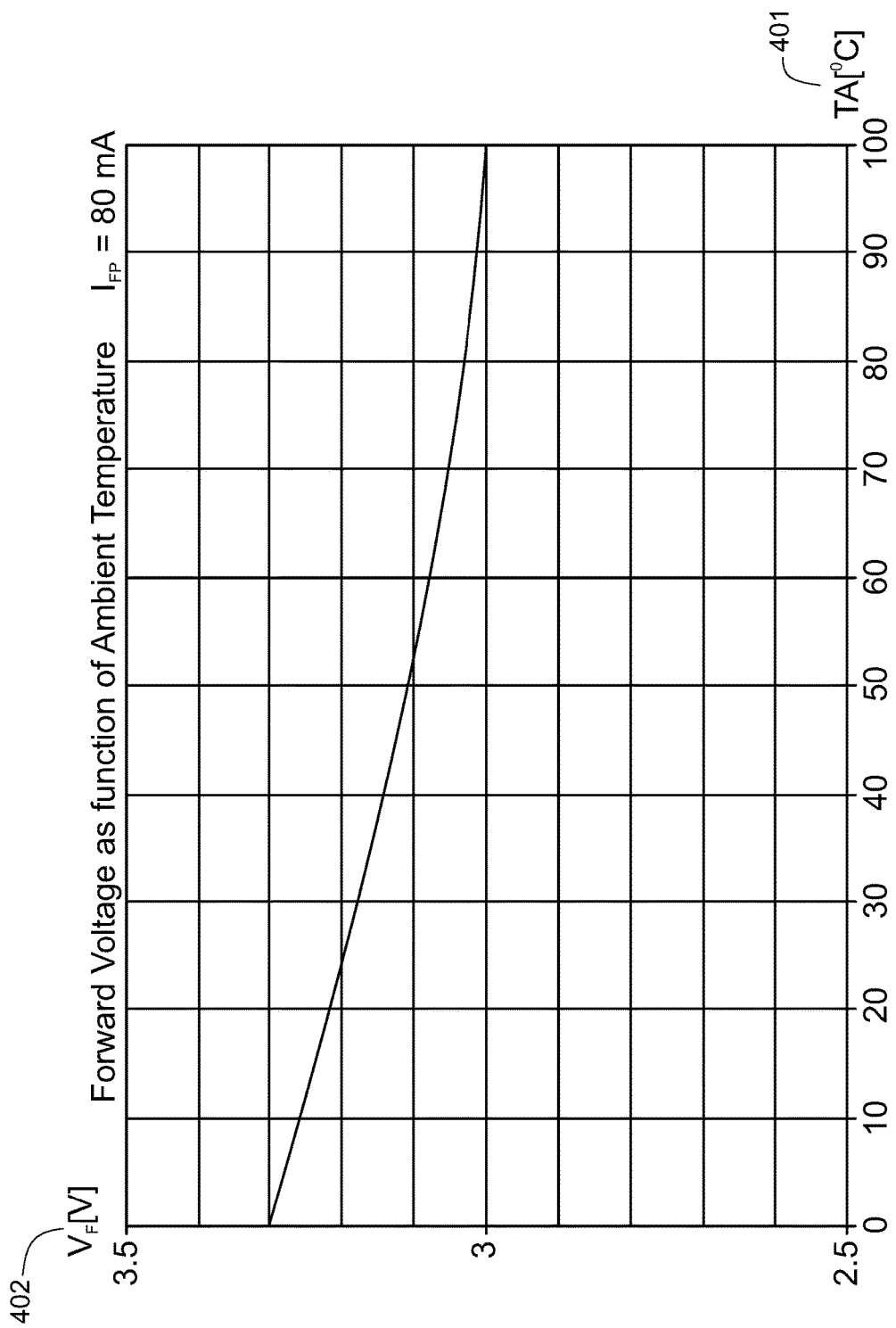
FIG. 4 illustrates an exemplary temperature-voltage curve for an LED.

FIG. 4 illustrates an exemplary temperature-voltage curve for an LED at a forward current ($I_{FP}$) of 80 mA. Referring to FIG. 4, as the ambient temperature Ta 401 rises, there is a corresponding decrease in the LED forward voltage Vf 402. It is seen that the typical slope of a Temperature-Voltage curve is $-1$ mV/° C.~$-3$ mV/° C., and varies with the forward current (If).

Figure 5:
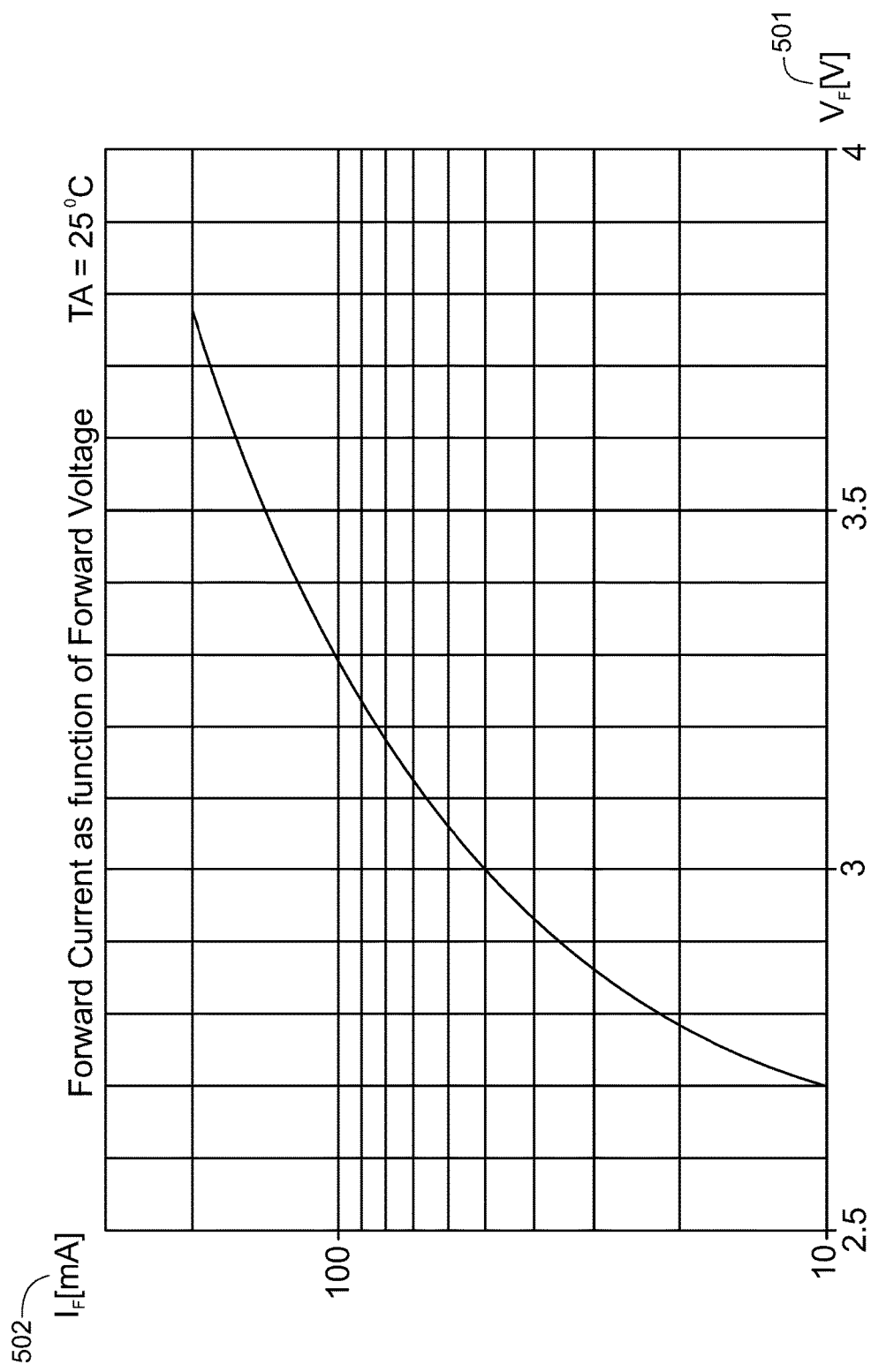
FIG. 5 illustrates an exemplary voltage-current curve for an LED.

FIG. 5 illustrates another curve showing the relationship between forward voltage Vf and forward current If, for a given ambient temperature Ta. Referring to FIG. 5, for a given ambient temperature of 25° C., forward voltage Vf 501 increases as forward current If 502 increases.

The methods of the present specification compute the mathematical relationship between the following variables: forward voltage Vf, forward current If, and ambient temperature Ta, to dynamically determine the junction temperature of an LED. Further, in an embodiment, the methods of the present specification determine the temperature of at least two, or all, of the LEDs in the distal tip and compute an average temperature to compensate for any errors in measurement which may arise due to using the LED as a temperature sensor.

Figure 6:
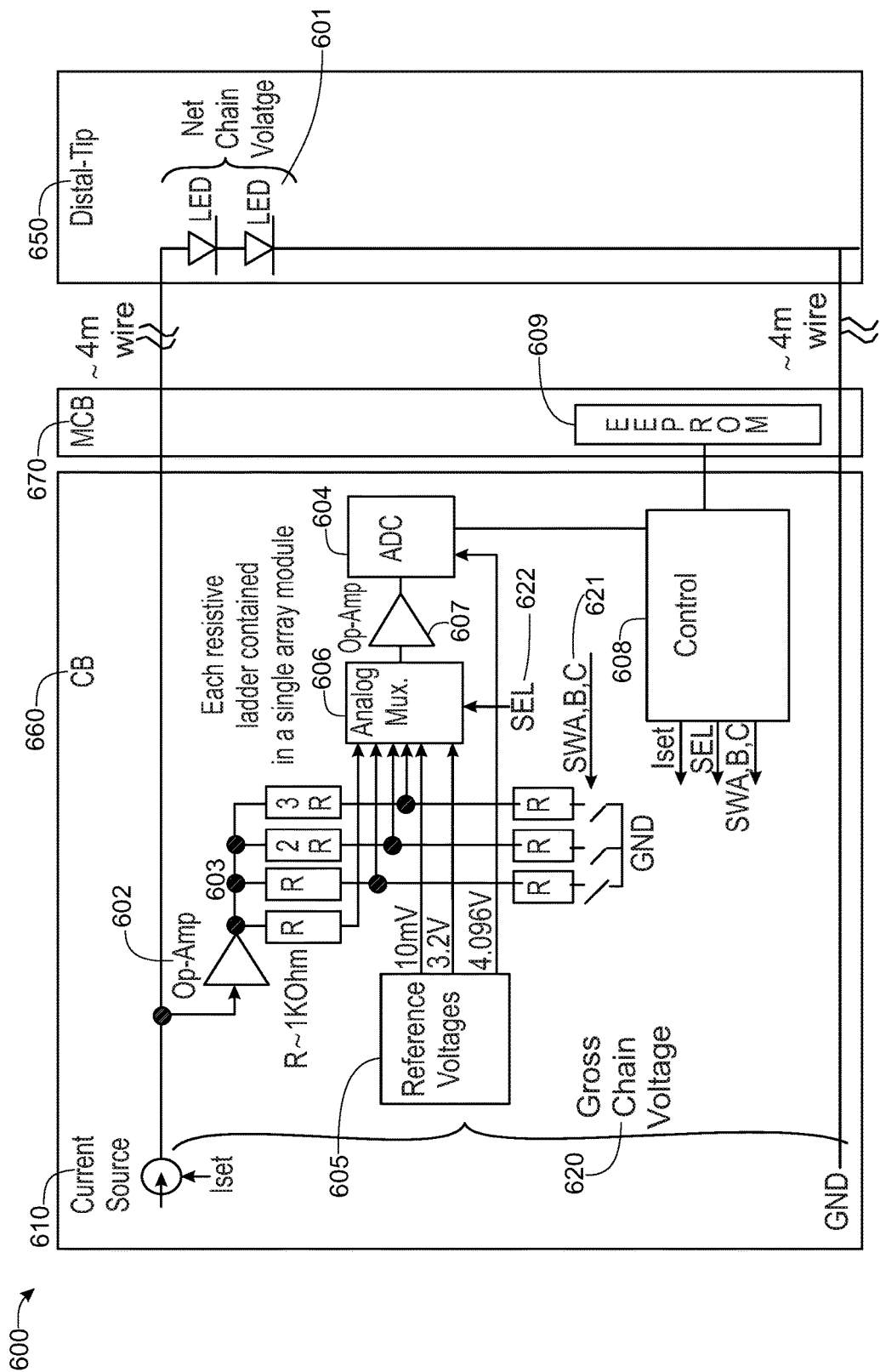
FIG. 6 illustrates an electrical circuit for measuring the temperature of a plurality of LED illuminators located in a distal tip section of an endoscope, in accordance with an embodiment of the present specification.

FIG. 6 illustrates an electrical circuit 600 for measuring the temperature of a chain of LED illuminators 601 located in the distal tip 650 of an endoscope. In an embodiment, the circuit is located on the camera board (CB) 660, which is a part of the controller (MCU) (216 in FIG. 2A) of the endoscope. In an embodiment, the main connector board (MCB) 670 is a miniature unit located in a proximal end of the endoscope itself and supports two main tasks requiring non-volatile memory (EEPROM) and a parallel-I2C I/O expander.

It may be noted that an endoscope with multiple viewing elements typically has at least a corresponding number of illuminators. For example, an endoscope with three cameras may have three chains of LEDs, each chain composed of several LEDs connected in series. In an embodiment, each chain of LEDs is in electrical communication with electrical circuit 600.

Referring to FIG. 6, the circuit comprises a first high precision, high voltage op-amp (operational amplifier) 602 in a voltage-follower configuration that buffers the voltage of the LED-chain and drives the resistive ladders 603 without drawing significant current from the chain 601. In an embodiment, the set of resistive ladders 603 comprises four resistive ladders, each being fed by the op-amp 602. In an embodiment, gains of the four resistive ladders are 1, ½, ⅓ and ¼, respectively and are designed to normalize the input of ADC (Analog to Digital Converter) 604 to be equivalent to that of a single LED in the chain of LEDs. In an embodiment, the input of ADC 604 is equivalent to that of a single LED, regardless of the number of LEDs in the chain. This ensures that the ADC's input does not exceed a permitted upper limit if a chain has more than one LED.

In an embodiment, the circuit further comprises a set of three accurate reference voltages 605. Exemplary values of reference voltages are 10 mV, 3.2V, and 4.096V, with an accuracy of at least 0.02%. In an embodiment, all reference voltages stem from a single source. In an embodiment, an analog multiplexer 606 is provided for selecting one of the resistive ladders and one of the reference voltages (10 mV or 3.2V) that feed the ADC 604, via second op-amp 607. In an embodiment, the above selection is made on the basis of the number of LEDs in series per chain. In an embodiment, this number is extracted from identification data stored in the EEPROM 609 of the MCB 670. In various embodiments, the chosen ladder as a function of LEDs in a chain is: 1 LED:1; 2 LEDs: ½; 3 LEDs: ⅓; and 4 LEDs: ¼. The third reference voltage (which is 4.096V as mentioned above) acts as the reference voltage for the ADC 604, which measures the voltage over the chain of LEDs 601. In an embodiment, ADC resolution is at least 16-bits, with zero-scale and full-scale errors each being of the order of lmV or better.

In an embodiment, N-Ch MOSFETS (not shown) are provided at the base of each resistive ladder, which switch on only the resistive ladder in use, thereby reducing op-amp load and heat dissipation. In an embodiment, resistors composing the resistive ladders are encapsulated in multi-resistor array modules to achieve highest precision (resistor-resistor tracking precision).

It may be noted that while the electrical circuit 600 for temperature measurement is in electrical communication with each chain of LEDs, some of the components may be used to serve more than one chain. For example, in an embodiment, a multi-channel ADC instead of a single channel ADC is used. Similarly, in embodiments, the control component 608 and EEPROM 609 are commonly employed for all chains. In an embodiment, EEPROM 609, or any other type of non-volatile memory installed in the endoscope's MCB (Main Connector Board) 670 is used for storing LED parameters and polynomials representing voltage-temperature relationship for different types of LEDs. This data is used for temperature measurement at the LED junctions. In an embodiment, the current source 610 is unique for every chain of LEDs. In various embodiments, the resistive ladders 603, analog to digital converter (ADC) 604, reference voltages 605, analog multiplexer 606, and second op-amp 607 are unique per chain. An advantage of having unique components for each chain is simultaneous reading of all chains resulting in better accuracy and reading speed. A disadvantage is the requirement for additional hardware, as each of said components is duplicated for each chain. In other embodiments, these components are shared by all chains. When the components are all shared, a first op-amp 602 must be proceeded by an analog multiplexer (not shown) to select which chain voltage should drive it at any given point in time. Whether or not components 603 through 607 are unique or shared, control component 608 is preferably shared by all chains, regardless of the number of chains, since there is only one inter-integrated circuit (I2C) bus connecting the EEPROM 609 with said control component 608 of the circuit board (CB) 660.

In an embodiment, assuming the current source 610 is accurate, LED chain current need not be measured, as it is practically identical to the set current (Iset). Components 602-607 form a system measuring the LED chain's voltage. Components 602-607 measure the "Gross Chain Voltage" 620. The controller (216 in FIG. 2A) subtracts the predicted resistive losses (estimated as the product of the wire and PCB resistance measured in an evaluation phase with the Iset current) from the gross chain voltage 620 to obtain the net forward voltage Vf. Once forward voltage Vf and forward current If are known, it is possible to calculate the junction temperature (Tj) based on data collected during the evaluation phase. As mentioned above, the current source 610 is not shared by the LED chains, the control component 608 is shared, and components 602 through 607 may be unique or shared in various embodiments.

In an embodiment, the control component 608 is commanded by the system-on-module (SOM), through the Base-Board FPGA and CB FPGA, to set each chain of LEDs to its own specific current Iset. Iset can be either a digital parallel word or a serial bus commanding the current Source 610 what current it should output. Alternately, Iset can be an analog voltage generated from within the control component 608 with a DAC. In an embodiment, Iset is a result of a physician choosing a specific illumination level and control component 608 must not alter it during the periodic temperature measurement. Hence, the temperature measurement must be transparent to the physician. Control component 608 is linked to EEPROM 609 with an I2C bus, and serves as a mediator between a parallel bus of address and data originating from the SOM and I2C. Among the plurality of data types passing from the EEPROM 609, is the information indicating how many LED chains exist, how many LEDs exist per each chain, LED vendor P/N, coefficients of polynomials (i.e. data used for evaluating the temperature). SW A, B, C signals 621 are optional and designed to cut off current from resistor ladders when inactive. SW A, B, C 621 are normally inactive, with only one of them, if any, becoming active during a temperature measurement. In an embodiment, during a temperature measurement, the activity of SW A, B, C is defined as: LED chain of one LED: none; LED chain of two LEDs: SW A; LED chain of three LEDs: SW B; and, LED chain of four LEDs: SW C. SEL 622 is a parallel bus instructing which input the "Analog Mux" 606 should choose. SEL 622 is aligned with SW A, B, and C 621 when measured voltage needs to be that of the resistive ladders 603. However, in an embodiment, SEL 622 has extra two combinations compared with SW A, B and C 621 which are for self-calibration measurements: 10 mV and 2.5 V. Control component 608 also interfaces the ADC 604 with a bus to command it to start a conversion sequence and to consequently read the conversion result. Said result is then passed on throughout CB's 660 FPGA fabric to SOM (via the Base-Board and its FPGA) or to a CB or BB FPGA-internal controller overseeing the temperature measurement.

Figure 7:
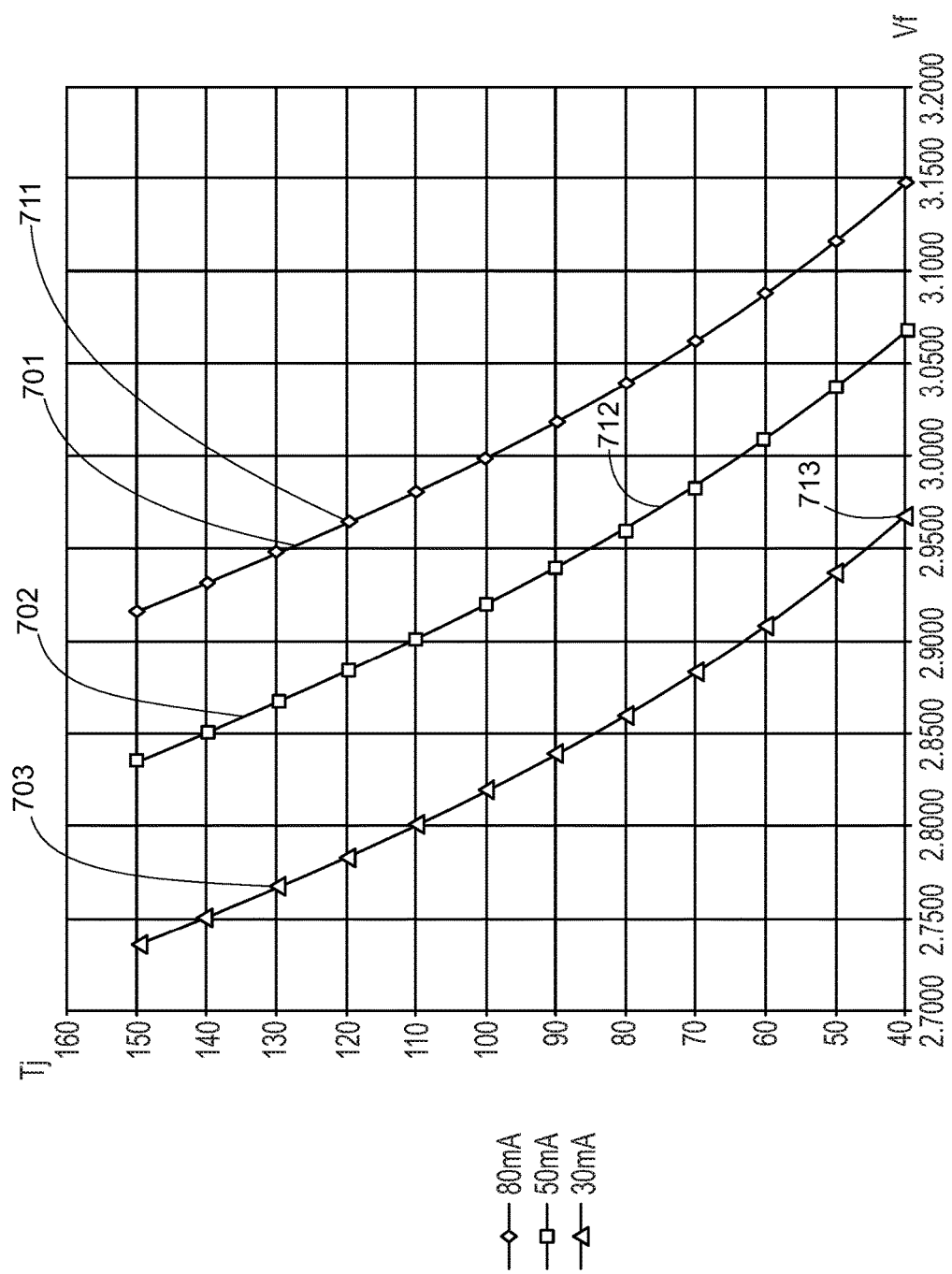
FIG. 7 illustrates a graph showing voltage-temperature curves for various forward currents for an exemplary LED.

As explained earlier, the relationship between forward voltage and junction temperature of an LED is known only for a specific forward current (If). FIG. 7 illustrates voltage-temperature curves 701, 702 and 703 for forward currents of 80 mA, 50 mA and 30 mA, respectively. One of ordinary skill in the art would appreciate that LED manufacturers normally do not provide the voltage-temperature relationship function over a broad range of currents, nor do they guarantee the tolerance if and when such a relationship is provided. Therefore, in an embodiment, the method of present specification provides a prototype evaluation process for every model of LED installed in the distal tip. The purpose of the process is to build for various values of current in a broad range, a function that best calculates a LED's junction temperature based on its voltage. This function may be computed for example, for currents ranging from 5 mA through 80 mA, in steps of 5 mA (i.e., 5, 10 . . . 80 mA).

Figure 8:
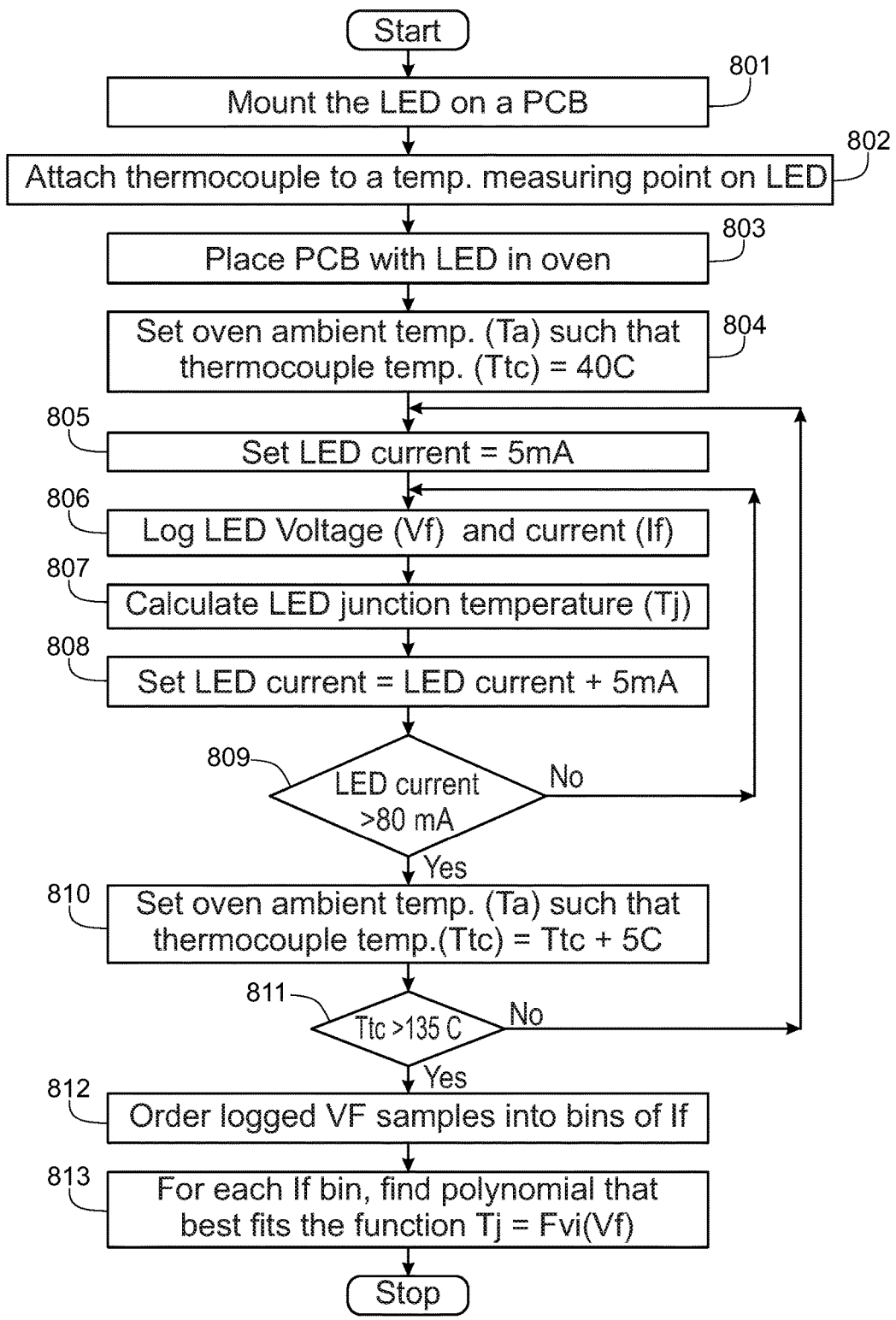
FIG. 8 is a flowchart illustrating an exemplary evaluation process and temperature-voltage function computation for a given LED, according to an embodiment of the present specification.

FIG. 8 is a flow chart showing the steps of an exemplary evaluation process and temperature-voltage function computation for a given LED that is used in the distal tip in accordance with an embodiment of the present specification. In an embodiment, the process is carried out manually, by an operator. Referring to FIG. 8, in the first step 801, the LED is mounted on a PCB, wherein the PCB is the same as normally used in the distal tip. Next, in step 802 a thermocouple is attached to a temperature measuring point defined by the LED manufacturer. For example, this point is defined as "Ts Point" in Nichia® LEDs, solder point in some Lumileds® LEDs, or thermal pad in other Lumileds® LEDs. Thereafter, in step 803, the PCB along with the LED is placed in an oven, with the thermocouple and LED current supply wires routed through the oven door. The following steps are then repeated for every thermocouple temperature in the range of 40 degrees C. to 135 degrees C. (or lower, in some LED models) in increments of 5 degrees C. (for example), as indicated by steps 804, 810 and 811. The oven ambient temperature (Ta) is adjusted such that the thermocouple (Ttc) temperature is desired and stable, as shown in step 804.

For a given Ttc, the subsequent steps are repeated for every current in the range 5 mA to 80 mA (for example) in steps of 5 mA (for example), as indicated by steps 805, 808 and 809. After setting the LED current to a desired value, LED voltage (Vf) and current (If) values are logged, as shown in step 806. Thereafter, in step 807, junction temperature of the LED, Tj is calculated as follows:

$P$ (approximate dissipated power of LED)=$Vf \times If$.

Then, for an LED with a "Ts Point" (Nichia®), for example: $Tj=Ttc+Rjs \times P$;

Where Rjs is junction-"Ts point" thermal resistance.

Again, for example, for an LED with a solder point defined as reference (Lumileds®):

$Tj=Ttc+Rjc \times P$;

Where Ttc is LED's case temperature and Rjc is junction-case thermal resistance.

After logging values of Vf, If and Tj for each LED current step and each desired thermocouple temperature (Ttc), all logged Vf samples are ordered into bins of LED currents (If), as shown in step 812. Then, per each If bin, operator finds the polynomial that best fits the function Tj =Fvi(Vf) for a specific If, as shown in step 813. The values for polynomial Fvi corresponding to all If bins are then stored in the EEPROM.

In an embodiment, the above process is repeated for LEDs of the same model but of older age and/or a longer operation history to determine how these factors affect the Voltage-Temperature curve.

Figure 9:
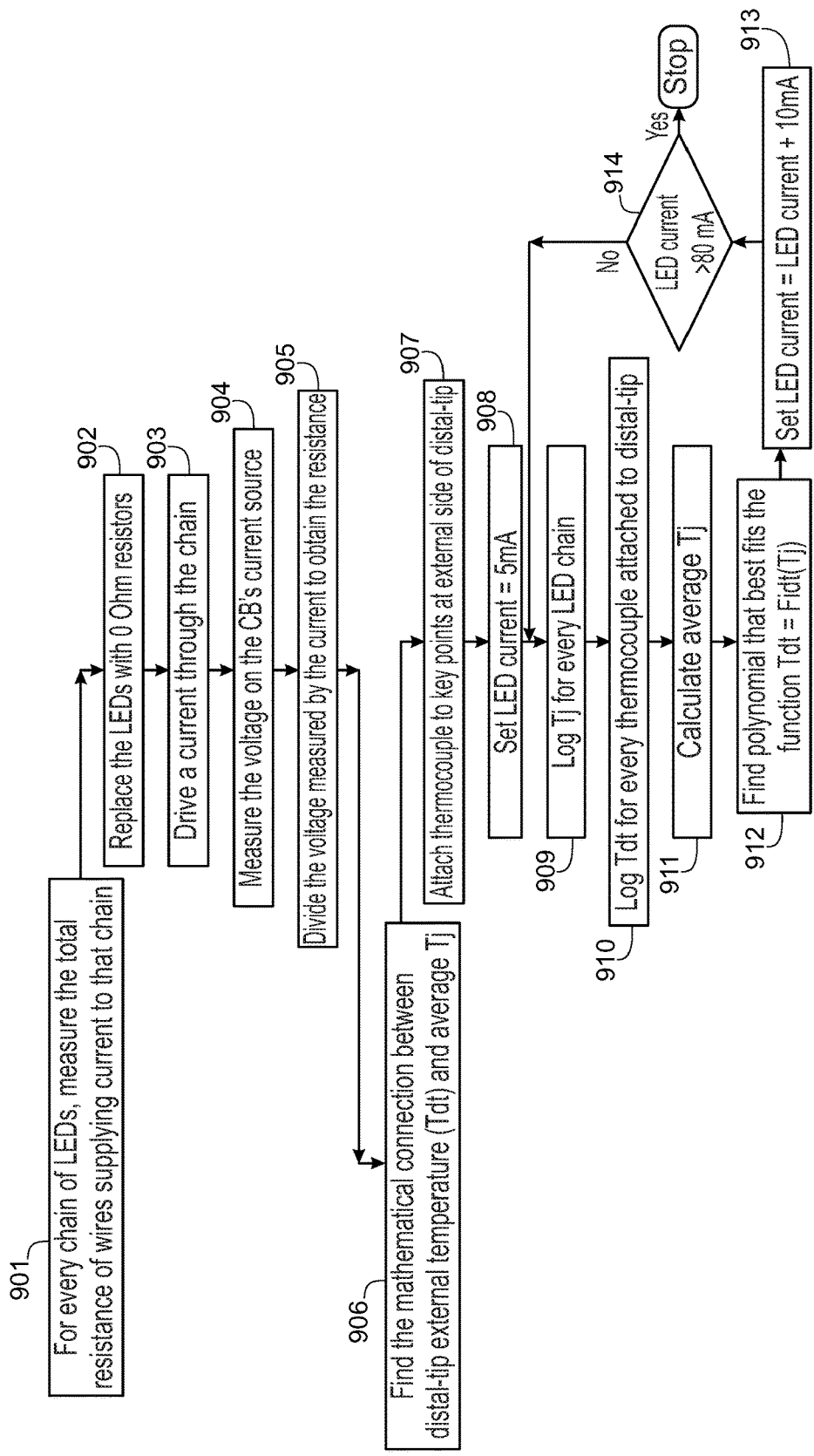
FIG. 9 is a flowchart illustrating an exemplary evaluation process for a given model of an endoscope, according to an embodiment of the present specification.

In an embodiment, an evaluation process is also carried out for every model of endoscope using a sample of endoscopes from that model. In some embodiments, the process described below also includes measuring the resistance of the wire running between the distal tip of the endoscope and the controller (216 in FIG. 2A) and the resistance of PCB traces, as these may vary between endoscope types. This process, in an embodiment, is carried out manually by an operator, and is illustrated by means of a flowchart in FIG. 9. Referring to FIG. 9, for every chain of LEDs within the endoscope under evaluation, the total (supply and GND) resistance of wires used to supply currents to that chain is measured, as shown in step 901. It should be noted that step 901, the measurement of resistance, comprises a series of sub-steps, with the first sub-step 902 comprising replacing the LEDs with zero Ohm resistors or wires in the sample endoscope. In the next sub-step 903, a current is driven through the LED chain, which is high enough to increase the accuracy of measurement, yet low enough to simulate practical LED currents. In the next sub-step 904, voltage on the current source located on the circuit board of the endoscope is measured. This voltage is the total resistive loss of distal tip PCB, wires, connectors, and the camera board. In the next sub-step 905, the voltage measured in the previous step is divided by the current, to obtain the resistance. The value of total resistance helps in computing resistive voltage drop across the LED chain, and in calculating the net chain voltage, Vf. This is described in further detail below with respect to FIG. 10. One of ordinary skill in the art would appreciate that compensating for the total resistance (of wires, connectors, etc.) is important for accurate measurement of voltage, and hence, temperature at the LEDs.

In step 906 of the evaluation process, the mathematical connection between the distal tip external temperature (Tdt) and average Tj (junction temperature of an LED) is computed. For measuring the external temperature, in embodiments, thermocouples are attached to key points at external sides of the distal tip, as shown in 907. Thereafter, a series of sub-steps are executed, which are repeated for every current in the range 5 mA to 80 mA (for example) in incremental steps of 10 mA (for example), as shown by sub-steps 908, 913 and 914. After setting the LEDs' current to the desired value, Tj is logged for every LED chain, using the method described in FIG. 8, as shown in sub-step 909. Then in sub-step 910, Tdt is logged for every thermocouple attached to the distal tip. Thereafter average Tj is calculated in step 911.

In an embodiment, sub-steps 909, 910, and 911 are repeated for every cooling scheme that the endoscope system provides. For example, pressurized gas flow flowing out through the tip of an endoscope during a procedure is used to inflate the intestine, which prevents collapse of the intestinal walls on the endoscope, hence assisting in prevention of injuries, navigation, and observation. This gas flow also contributes to distal tip cooling since it is a means of forced convection heat dissipation. Thus, in an embodiment, the aforementioned steps are repeated for various levels of gas flow, such as 0% gas flow, 33% gas flow, 66% gas flow, and 100% gas flow. The steps are also repeated for the situation when water jets are employed along with 100% gas flow.

Finally, in step 912, the polynomial that best fits the function Tdt=Fidt(Tj) for the given LEDs' current is determined.

In an embodiment, for every endoscope manufactured, the endoscope's EEPROM is programmed with at least one of, and preferably a combination of, the following parameters:

Date of manufacture;

For every current measured, and per every point on the distal tip, a set of polynomial coefficients describing Tdt=Fidt(Tj) for the specific current and point on the distal tip;

Number of LED chains;

For each LED chain, the resistance of wires, number of LEDs in the chain, whether each LED is realized as single LED, or two LEDs connected in parallel, model ID of LEDs; and For each value of current used in the prototype evaluation process, the value of current, set of polynomial coefficients describing Tj=Fvi(Vf) (i.e., junction temperature vs. voltage, per given value of current).

In an embodiment, when an endoscope is in operation, the controller of the endoscope system periodically programs the endoscope's EEPROM with the elapsed operation time per each LED, categorized into illumination intensity bins. This logging of operational profile (or working age) of LEDs can assist in real time fitting of the Voltage-Temperature curve according to any given time, by knowing the operational profile up to that specific point of time. Further, measurements done for a newly assembled distal tip can be repeated for an aged distal tip of known operational profile, to investigate how aging and accumulating operational hours affect the Voltage-Temperature characteristics of the distal tip.

In an embodiment, for every endoscope it is verified that measuring the distal tip temperature at predetermined select setup conditions of temperatures and currents using the present method approximates well with measuring with an external thermocouple.

In an embodiment, the system uses BIT (Built-In Test) for its ADCs (Analog-to-Digital Converters, described earlier with reference to FIG. 6) by channeling the precise voltage references to inputs of ADCs and then verifying that readouts are within permitted tolerances. In an embodiment, such Built-In Tests are performed once upon system power-up. Further, in an embodiment, if ADCs are suspected of not meeting with the rated accuracy, the system periodically self-calibrates using the following relationships:

For every ADC, the ideal relationship between N (digital readout) and Vin (input voltage) is: Vin=A×N +B; where A and B are coefficients representing gain and offset respectively. The closer A is to the ideal theoretical gain, the more accurate the ADC. Additionally, the closer B is to zero, the more accurate the ADC.

The ADC is calibrated with up-to-date A and B coefficients, using the following equations:

$$A=(V2-V1)/(N2-N1) \text{ and}$$

$$B=(V1 \times N2 - V2 \times N1)/(N2-N1);$$

Where V1=Lower reference voltage,

V2=Higher reference voltage,

N1 is obtained by channeling the lower reference voltage V1 to ADCs' inputs, and obtaining an average of a few readouts, and N2 is obtained by channeling the higher reference voltage V2 to ADCs' inputs and obtaining an average of a few readouts.

Figure 10:
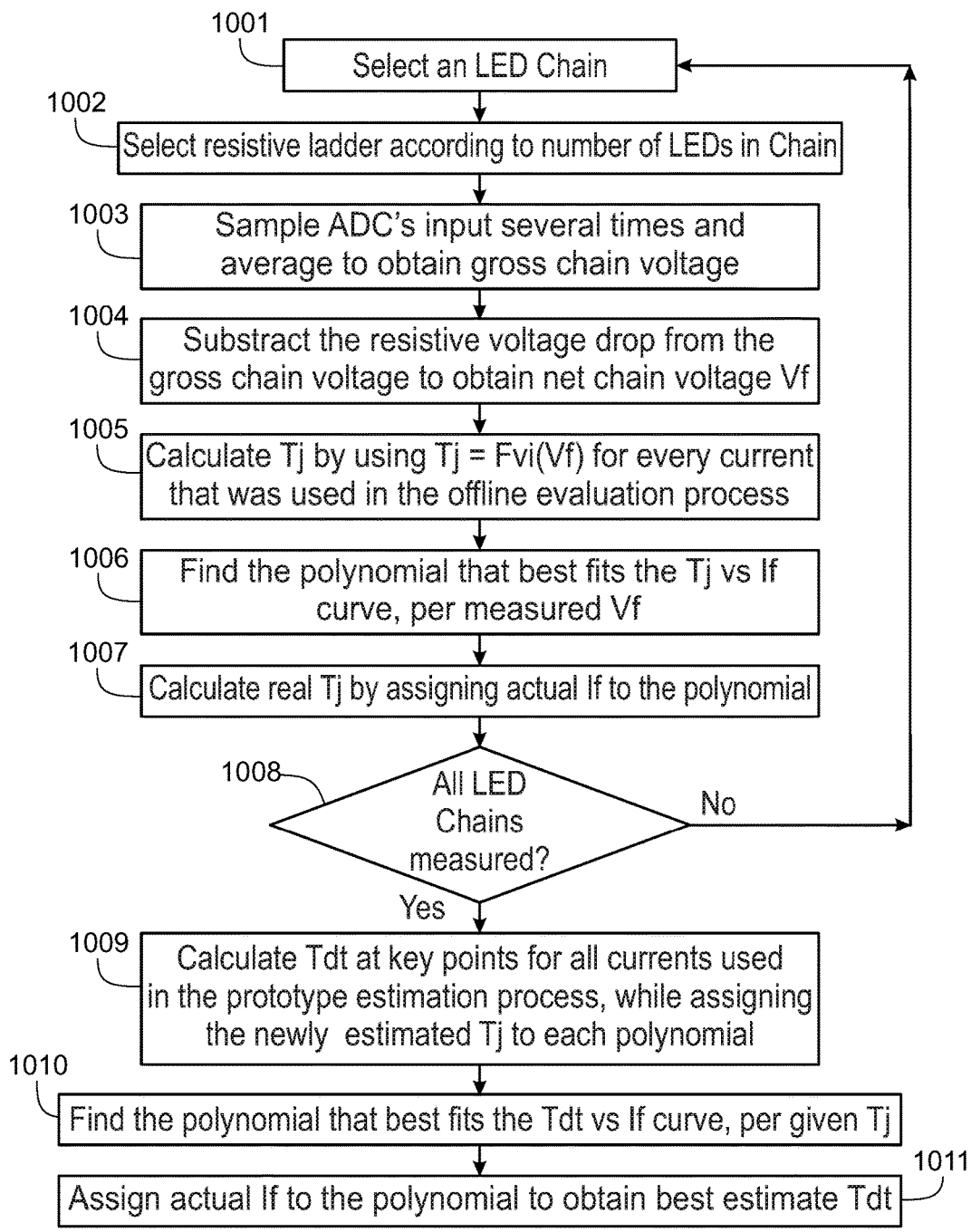
FIG. 10 is a flowchart illustrating the process of temperature determination during a real-time procedure, according to an embodiment of the present specification.

In an embodiment, the controller of the endoscopy system is configured to automatically determine the LEDs' junction temperature (Tj) and distal tip's temperature (Tdt) when the endoscope is in operation. The temperature determination is based on the measurement of LED voltages, as described above with reference to FIGS. 6, 7, 8, and 9. FIG. 10 illustrates the process of temperature determination according to an embodiment, using a flowchart. Referring to FIG. 10, along with FIGS. 6, 7, 8, and 9, in the first step 1001, an LED chain is selected for voltage measurement. Next, in step 1002, the system selects an appropriate resistive ladder (shown in FIG. 6) according to the number of LEDs in the chain being measured. This information is retrieved from the EEPROM. The resistive ladder normalizes the ADC's reading to be always equivalent to a single LED and also prevents ADC input from exceeding permitted voltage.

To obtain a good accuracy and noise level, the input of ADC is sampled and then averaged, as shown in step 1003. The average result represents the gross chain voltage, which includes all resistive voltage drops, mainly due to endoscope wires. Next, in step 1004, the resistive voltage drop is subtracted from the gross chain voltage to obtain the net chain (LED) voltage Vf. It may be noted that the resistive voltage drop is the product of three factors:

1. Electric current being supplied to the LED chain, which is known to the system since the system itself regulates that current;
2. Resistance of the LED chain (mainly due to wires), which is stored in the EEPROM; and
3. 1/[number of LEDs per chain]. The number of LEDs per chain is specified in the EEPROM.

After determining net chain voltage Vf, LED's junction temperature (Tj) is calculated for all currents used in the prototype evaluation process (detailed in FIG. 8), using the newly calculated Vf. This Vf can be considered the average Vf over all LEDs in a chain. This is shown in step 1005. Calculation of Tj is based on the set of polynomials coefficients stored in EEPROM, describing Tj=Fvi(Vf), for every current.

With all the junction temperatures obtained from calculating the polynomials at all defined currents, per measured Vf, in the next step 1006 the polynomial that best fits the Tj vs. If curve (per the given measured Vf) is computed. Thereafter, the real Tj is calculated in step 1007 by assigning the actual If value to the polynomial computed above. The actual If implies the value of current being supplied at that time, instead of any of fixed If as used in the prototype evaluation process. It may be noted that in case of two LEDs operating in parallel, actual current value assigned to polynomial is If/2. Referring again to FIG. 7, the LEDs of an exemplary system are evaluated at 30 mA 703, 50 mA 702, and 80 mA 701. In an embodiment, assuming the system detects a measured Vf of 2.970 V, Tj equals 40° C. 713 at I=30 mA, Tj equals 76° C. 712 at I=50 mA, and Tj equals 120° C. 711 at I=80 mA. Using these three data points, a Tj vs. If trendline can be extracted. Further assuming actual If is 45 mA, the actual (real) Tj can be determined by interpolating the three data points. Although three data points are described in the current example, the process will use a much greater number of data points to determine Tj.

The above steps (1001 through 1007) are repeated as previously for all the LED chains in the distal tip, as illustrated by step 1008.

After the Tj (junction temperature) for all the LED chains is measured, the system estimates external temperature (Tdt) at all the key points on the distal tip, which were earlier measured during the prototype evaluation process, described with reference to FIG. 9. For this purpose, in step 1009, Tdt is calculated for all currents used in the prototype estimation process, while assigning the newly estimated Tj to each polynomial. Coefficients of these polynomials are stored in the EEPROM. Next, in step 1010, the polynomial that best fits the Tdt—If curve for the given Tj is computed. In one embodiment, the relationship between Tdt and Tj is defined as Tdt=If×K+Tj+Offset. In some embodiments, this relationship is further affected by the number of LED chains and by the dissipation of the constant heat of the imagers.

In the next step 1011, the actual If is assigned to the polynomial computed above to obtain the best estimate for distal tip temperature at that key point. The actual If implies the value of current being supplied at that time, instead of any of fixed If as used in the prototype evaluation process.

In an embodiment, the system displays the measured temperature on the endoscope display. In various embodiments, the temperature displayed is the Tj, Tdt, or both.

In an embodiment, the system automatically takes one or more corrective actions to resolve overheating in LEDs or in the distal tip exterior. Overheating conditions are reflected by the average Tj (for LEDs) or average Tdt (distal tip) being too high. For Tj, overheating includes temperatures too close to the maximum Tj permitted by the LED manufacturer (absolute maximum rating) and, in some embodiments, is equal to 120° C. For Tdt, overheating includes temperatures considered unsafe or uncomfortable for the patient. Corrective actions may include, but are not limited to:

Reducing dissipated heat by reducing LED currents in chains where overheating occurred, or by switching off currents in the chains being overheated (excluding chains related to front viewing element);

Intensifying cooling by autonomously increasing endoscope gas flow and/or by activating water jets.

In an embodiment, an icon is displayed on the endoscope system screen recommending the physician to activate the water jets. In one embodiment, an icon or notification indicating that temperature is being optimized is displayed on the screen in case any of the above corrective actions are taken, including current being reduced or switched off and increasing cooling.

In one embodiment, an overheating event is logged in system log file.

In an embodiment, after Tj/Tdt return to nominal levels after taking corrective measures for overheating, the system applies a hysteresis mechanism when restoring intended system settings, such as LED currents. This mechanism prevents oscillation and annoying image artifacts. The hysteresis mechanism defines different thresholds for different scenarios. For example, in an embodiment, the threshold for setting a low value If to avoid overheating is 120° C. and a threshold for returning If to the normal setting is 110° C.

Figure 11:
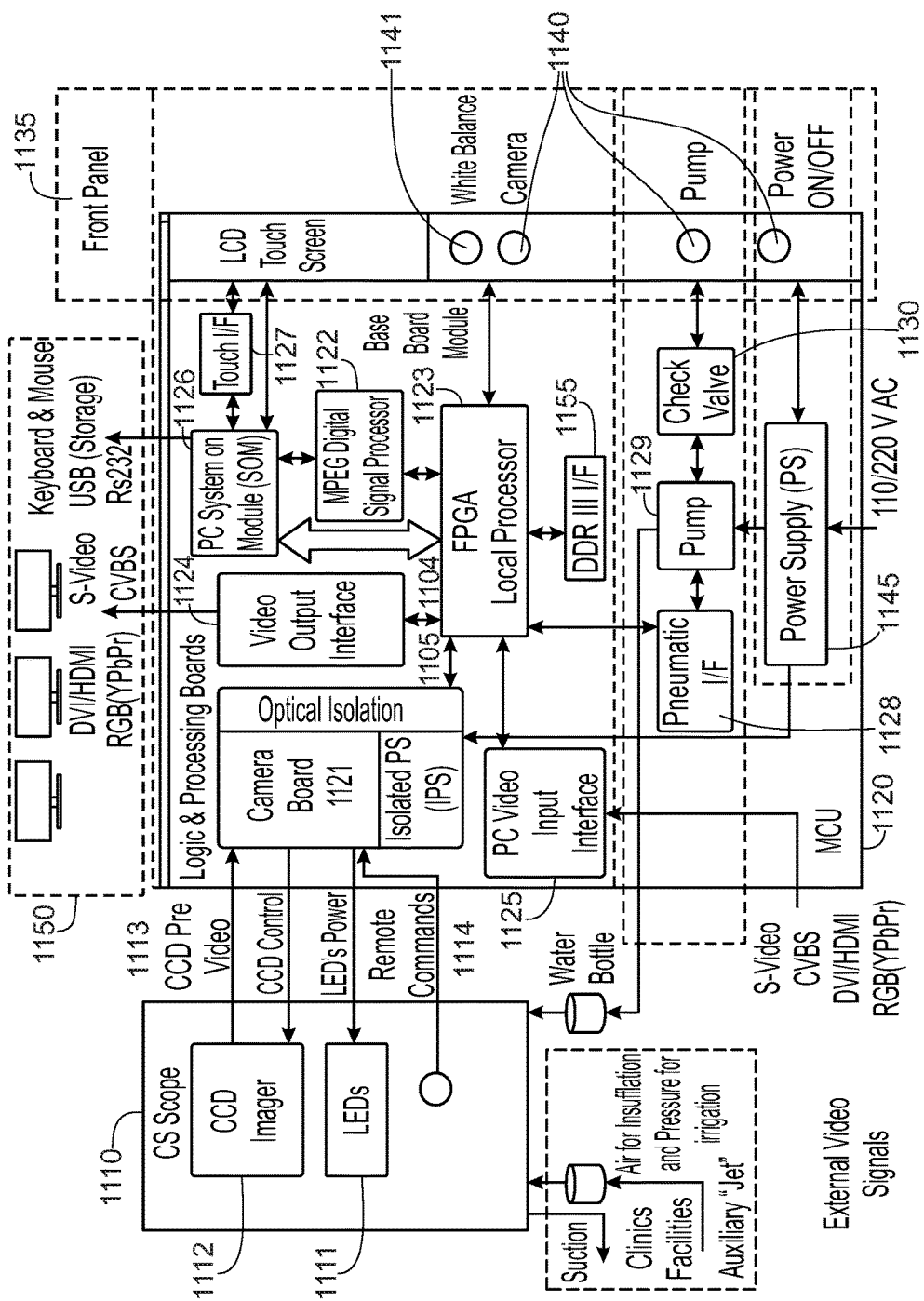
FIG. 11 depicts a block diagram of the control hardware for a multiple viewing elements endoscopy system, according to an embodiment of the present specification.

FIG. 11 details the controller hardware that is used for computation of temperature according to the methods detailed above, and also for taking corrective action in case of overheating in accordance with an embodiment of the present specification. Referring to FIG. 11, the controller circuit board 1120 of the Main Control Unit operatively connects with the endoscope 1110 and the display units 1150. In an embodiment, the controller circuit board 1120 further comprises a camera board 1121 that transmits appropriate commands to control the power supply to the LEDs 1111 and to control the operation of image sensor 1112 (comprising one or more viewing elements), such as but not limited to a Charge Coupled Device (CCD) or a Complementary Metal Oxide Semiconductor (CMOS) imager, in the endoscope. The camera board in turn receives video signal 1113 generated by the CCD imager and also other remote commands 1114 from the endoscope. The circuit for measuring voltage across the LEDs, shown and detailed with reference to FIG. 6, is also located on the camera board 1121.

In embodiment, the controller circuit board 1120 further comprises elements for processing the video obtained from the imager 1112, including MPEG Digital Signal Processor 1122, field-programmable gate array (FPGA), local processor 1123 that performs video interpolation and on-screen display overlay. The video signal is sent for display through Video output interface 1124. A video input interface 1125 is also provided for receiving video input from an external analog or digital video source.

FPGA 1123 is a logic device programmed specifically for system requirements and is associated with memory, such as DDR 1155. In an embodiment, the pre-programmed instructions from the FPGA 1123 are executed by Video output interface 1124 to generate appropriate video signals for display. FPGA 1123 performs tasks that may be categorized in two types: logic tasks which must be implemented by hardware (as opposed to software), and logic tasks related to video image processing. In an embodiment, FPGA is programmed to compute LED junction temperature and distal tip temperature, in accordance with the method detailed in FIG. 10. In some embodiments, these calculations are performed in the SOM 1126, but can also be assigned to an FPGA on the camera board 1121 or the FPGA 1123 on the base-board. FPGA 1123 is further programmed to take corrective actions in case of overheating, such as reducing LED currents and increasing cooling by using water jets or gas.

System on Module (SOM) 1126 provides an interface to input devices such as keyboard and mouse, while Touch I/F 1127 provides touch screen interface. In an embodiment, the controller 1120 further controls one or more fluid, liquid and/or suction pump(s) which supply corresponding functionalities to the endoscope through pneumatic I/F 1128, pump 1129 and check valve 1130. In embodiments, the controller further comprises a power supply on board 1145 and a front panel 1135 which provides operational buttons 1140, 1141 for the user.

The camera board 1121 receives video signal 1113 which, in an embodiment, comprises three video feeds, corresponding to video pickups by three endoscopic tip viewing elements (one front and two side-looking viewing elements), as generated by the CCD imager 1112.

Figure 12A:
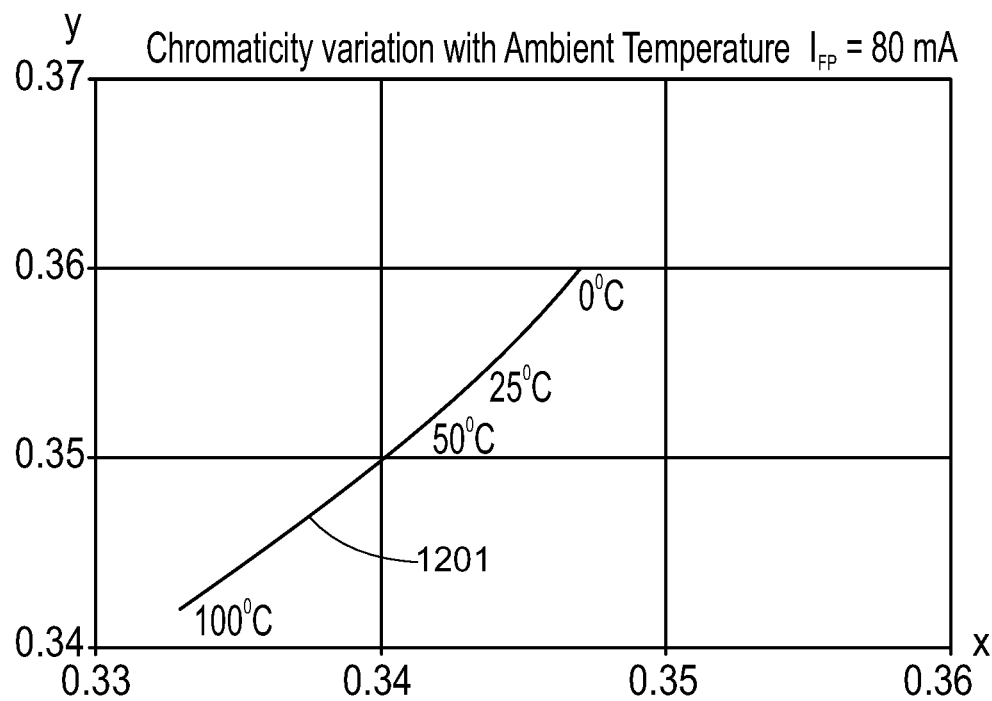
FIG. 12A is a graph illustrating the effect of ambient temperature on the chromaticity coordinate.
Figure 12B:
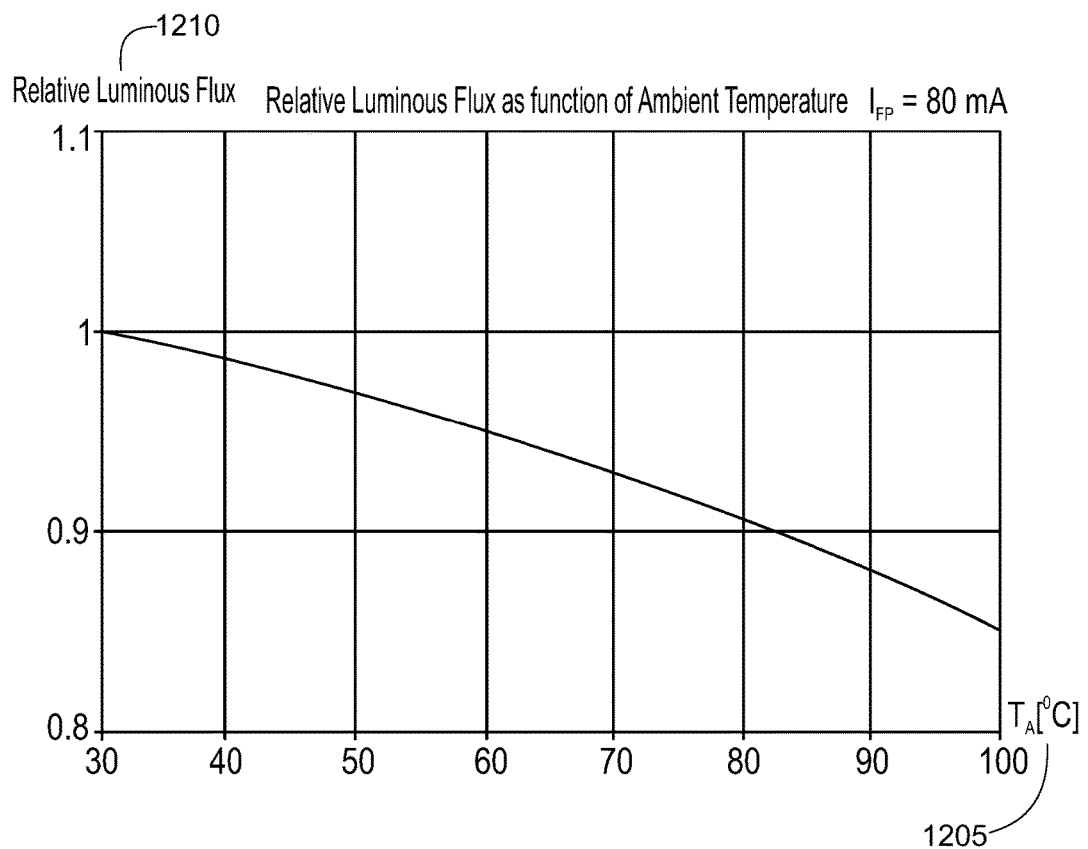
FIG. 12B is a graph illustrating the effect of ambient temperature on luminous flux.

In an embodiment, the system adaptively configures image processing parameters according to measured temperatures at the distal tip, to achieve optimal image quality, regardless of whether overheating occurs or not. FIG. 12A shows a graph illustrating the effect of ambient temperature on LED chromaticity coordinate, which can affect imager chromaticity. Referring to FIG. 12A, it can be seen from the curve 1201 that for a given forward current (which is 80 mA in the present example), as the ambient temperature increases, chromaticity shifts more toward blue. Another graph in FIG. 12B shows the relationship between LED ambient temperature $T_A$ 1205 and LED relative luminous flux 1210, which is an indicator of brightness. Variations in LED luminosity can affect image luminosity. As seen in the figure, as the ambient temperature approaches 30° C. and then increases further, for a given forward current (which is 80 mA in the present example), the luminous flux starts decreasing. Therefore, in an embodiment, image parameters are altered to compensate for possible changes in brightness, chromaticity and noise, which may occur due to change in temperature of the LED illuminators. This tuning of parameters is effectuated by the hardware components detailed above with reference to FIG. 11.

In accordance with another embodiment, the present specification discloses a method to automatically regulate, control or manage the illumination, luminance or luminous intensity of the one or more illuminators associated with each of the plurality of viewing elements of the endoscope tip section. The terms illumination intensity, luminance intensity or luminous intensity are hereinafter used interchangeably as an expression of the amount of light power emanating from an LED and in various embodiments is a function of electric current flow through the LED.

In an embodiment, the luminance intensity of one or more illuminators is automatically regulated depending upon whether the endoscope tip section is detected to be in an active or passive state. In various embodiments, the active state corresponds to at least one of the following scenarios: a) a movement of the endoscope tip section relative to its surroundings, environment or background, indicative of, for example, a use of the endoscope tip section in a typical endoscopic procedure, and/or b) an object approaching or being brought at a distance of less than a predefined threshold value of distance from the endoscope tip section. In an embodiment, an active state for the tip section is defined as having an object approach or brought toward the tip section of the endoscope at a distance of less than or equal to 5 centimeters (d≤5 cm) from the endoscope tip section. In various embodiments, a passive state corresponds to a scenario where the endoscope tip section is stationary or static relative to its surroundings, environment or background. That is, the endoscope tip section is static or not moving or one or more objects in the surroundings relative to the tip section may move so long as they remain beyond a predefined distance from the endoscope tip section.

In an embodiment, the method of the present specification automatically monitors and detects the active or passive state of the endoscope tip section and, in response, automatically regulates the luminance intensity of the one or more illuminators. In various embodiments, when the endoscope tip section is in the active state, the luminance intensity of the one or more illuminators is automatically set to a first intensity level. In some embodiments, the first intensity level corresponds to a default operating intensity level or to an intensity level manually set by a physician as per his preference. In various embodiments, the first intensity level corresponds to electric current flow, through one or more illuminators, ranging from about 20 mA to 100 mA, and more preferably 40 mA to 50 mA.

In various embodiments, when the endoscope tip section is in a passive state, the luminance intensity of the one or more illuminators is automatically set to a second intensity level. The second intensity level is either default intensity or manually set by the physician as per his preference. In various embodiments, the second intensity level is lower than the first intensity level. In some embodiments, the second intensity level is such that at this second intensity the one or more illuminators generate substantially lower heat in the endoscope tip section while still enabling the one or more illuminators to be illuminated and identifiable to indicate to the physician that the one or more illuminators are functioning. In some embodiments, the second intensity level corresponds to zero intensity which means that the one or more illuminators are switched off at the second intensity level. In various embodiments, the second intensity level corresponds to electric flow, through one or more illuminators, ranging from about 0 mA to 19 mA, and more preferably, 0 mA to 2 mA.

In an embodiment, the first and second intensity levels are different for each of the illuminators present in the system.

In accordance with various embodiments, the method of the present specification enables proximity detection by sensing the endoscope tip section to be in the active state when at least one object from the surroundings, environment or background approaches or is brought near the endoscope tip section at a distance of less than a predefined threshold value of distance 'd'. This proximity detection feature is advantageous since the physician can activate or set the one or more illuminators to the first intensity level by simply bringing their hand within the distance 'd' of the one or more illuminators without physically contacting the illuminators. In some embodiments, the proximity detection feature is enabled by default and can be disabled if needed. In some embodiments, the proximity detection feature can be enabled or disabled manually.

Figure 13A:
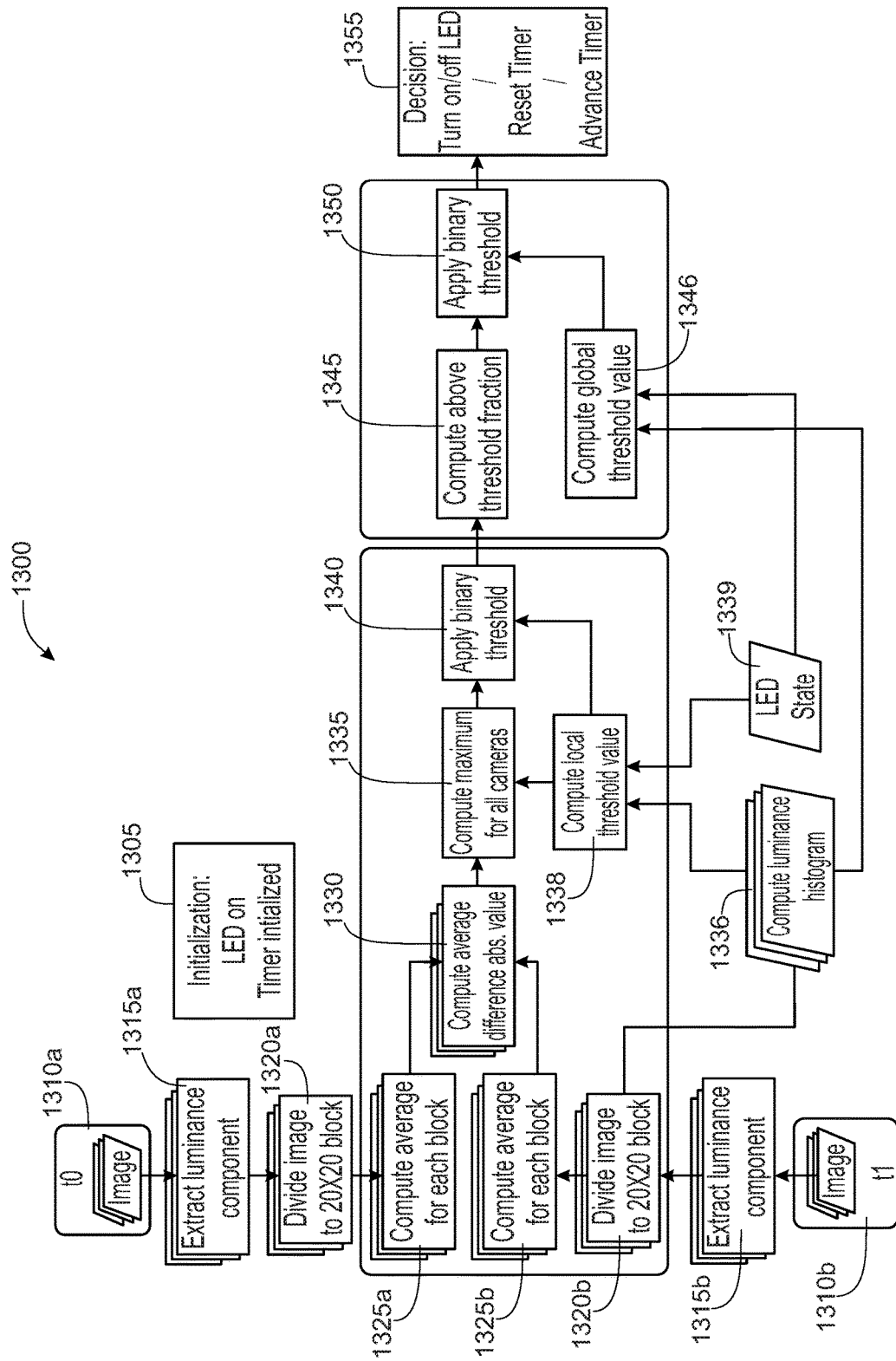
FIG. 13A is a flow chart illustrating a plurality of steps of a method of regulating illumination intensities of one or more illuminators of an endoscope tip section, according to certain embodiments of the present specification.

Reference is now made to FIG. 13A which is a flow chart illustrating a plurality of exemplary steps of a method 1300 of automatically detecting the active or passive state of the endoscope tip section (such as the tip section 230 of FIG. 2C) and accordingly regulating the luminance intensity of one or more illuminators, associated with a plurality of viewing elements of the endoscope tip section, to the first or the second intensity level. Persons of ordinary skill in the art should appreciate that the sequence of steps of the method 1300 are only exemplary and the sequence may change in alternate embodiments. In various embodiments, the method 1300 is implemented as software or a plurality of programmatic codes executed by a processor of a Main Control Unit, such as the MCU 216 of FIG. 2A, associated with the endoscope tip section.

In an embodiment, the method 1300 assumes an initialization stage 1305 where the one or more illuminators are switched on and a programmatic timer or counter is also initialized. At step 1310a, when the timer or counter is at a first time instance value such as $t_0$, a first sample is acquired of at least one image generated by the plurality of viewing elements of the endoscope. In one embodiment, the endoscope tip section includes three viewing elements—a front pointing viewing element, a first side pointing viewing element and a second side pointing viewing element (as shown in the tip section 230 of FIG. 2C). Thus, in this embodiment, at least one and up to three corresponding images are generated or captured by the three viewing elements. It should be appreciated that in various alternate embodiments with the endoscope tip section comprising one or two viewing elements the number of corresponding images generated are at least one and up to two. In a preferred embodiment, the first sample includes three image frames corresponding to three viewing elements of the endoscope tip section.

At step 1315a, luminance (Y) component is extracted for the pixels of each of the images (such as three images corresponding to three viewing elements in one embodiment) of the first sample captured at time $t_0$. At step 1320a each of the images, of the first sample, is divided or segmented into a plurality of blocks of n x m pixels. In an embodiment, each block is of size 20×20 pixels, yet block size may be smaller or larger than 20×20 pixels. Thereafter, at step 1325a, an average luminance for each block is calculated for each image of the first sample.

At step 1310b, when the timer or counter is at a second time instance value such as $t_1$, a second sample is acquired of at least one image generated by the plurality of viewing elements of the endoscope. In an embodiment, the second sample includes three image frames corresponding to three viewing elements of the endoscope tip section. In an embodiment, the time difference between $t_0$ and $t_1$ is about 0.5 seconds, yet the time difference between $t_0$ and $t_1$ may be smaller or larger than 0.5 seconds. In the embodiment wherein the time difference between $t_0$ and $t_1$ is about 0.5 seconds, every 15th image frames are sampled (assuming 30 frames per second as the frequency of frames). Next, at step 1315b, luminance (Y) component is extracted for the pixels of each of the images (such as three images corresponding to three viewing elements in one embodiment) of the second sample captured at time $t_1$. At step 1320b each of the images, of the second sample, is divided or segmented into a plurality of blocks of n×m pixels. In an embodiment, each block is of size 20×20 pixels, yet block size may be smaller or larger than 20×20 pixels. Thereafter, at step 1325b, an average luminance for each block is calculated for each image of the second sample.

Now, at step 1330 for each block an average luminance absolute difference or change is calculated between the corresponding images of the first and second samples (obtained at $t_0$ and $t_1$). In accordance with an embodiment, the average luminance absolute difference or change is calculated for each block of all three images obtained from the three viewing elements in the first and second samples. At step 1335, for each block, the maximum of the average luminance absolute difference or change is chosen from among the three sets of images obtained from the three viewing elements. At step 1336, a luminance histogram is computed as a count of the number of pixels for each luminance value in a represented range, such as 0 to 255 in case of 8 bits pixel representation.

Next at step 1340, for each block, the value of maximum average luminance absolute difference or change is compared against a first threshold luminance value, also referred to as a local threshold to determine or identify those blocks whose maximum average luminance change exceeds the first threshold luminance value. At step 1345, a count of the blocks is computed for which the maximum average luminance absolute difference value is found to exceed the first or local threshold or, alternately, a fraction is computed of such blocks with reference to the total number of blocks of step 1340. It should be appreciated that the first threshold luminance value or the local threshold is determined based on calibration and is dependent upon a plurality of factors such as, but not limited to, the type of image sensor (CCD or CMOS), number of pixels in the image sensor, size of pixels in the image sensor, type of illuminators (white light LED, an infrared light LED, a near infrared light LED, an ultraviolet light LED or any other LED), type of endoscope (colonoscope, gastroscope or bronchoscope).

Finally, at step 1350, the count or fraction of the blocks (for which the maximum average luminance absolute difference value is found to exceed the first or local threshold) is compared against a second threshold count, amount or fraction of blocks, also referred to as a global threshold. Depending upon whether the count or fraction of blocks does or does not exceed the second or global threshold, a decision (described further with reference to FIG. 3B) is made at step 1355 of at least whether the luminance intensity of the one or more illuminators should or should not be automatically changed from the first intensity level to the second intensity level or vice versa. It should be appreciated that the second threshold count or the global threshold is determined based on calibration and is dependent upon a plurality of factors such as, but not limited to, the type of image sensor (CCD, CMOS, number of pixels, size of pixels, etc.), type of illuminators (white light LED, an infrared light LED, a near infrared light LED, an ultraviolet light LED or any other LED), type of endoscope (colonoscope, gastroscope or bronchoscope),In various embodiments, the first and second threshold values are computed respectively, for example, at steps 1338 and 1346 based on the luminance histogram computed at step 1336 and by also taking into account the on/off state (referenced as 1339) of the one or more illuminators. It should be appreciated that the first or local threshold is computed for each block while the second or global threshold is computed for an entire image frame. In various embodiments, the first or local threshold is the number of pixels that have high luminance value as reflected in the luminance histogram. If the one or more illuminators is/are switched off then the first threshold is a substantially small value while the first threshold is a substantially large value if relatively higher number of illuminators are switched on. Similarly, the second or global threshold is the number, count or fraction of blocks that have high luminance value based on the luminance histogram. If the one or more illuminators is/are switched off then the second threshold is a substantially small value while the second threshold is a substantially large value if relatively higher number of illuminators are switched on.

It should be appreciated that in an embodiment, if the amount or fraction of blocks with luminance change (above the first or local threshold) is below the second or global threshold it is indicative that only a small portion of the images may have changed between the first and second samples. This indicates that the endoscope tip section is in passive state or is stationary relative to its surroundings, environment or background. That is, the endoscope tip section is static or not moving although one or more objects in its surroundings, environment or background may move—but remain beyond a predefined distance 'd' from the endoscope tip section. However, if the amount or fraction of blocks with luminance change (above the first or local threshold) is above the second or global threshold it is indicative that a sufficiently large part of the images have changed between the first and second samples. Thus, this indicates that the endoscope tip section is in active state as a result of at least one of the following scenarios: a) a movement of the endoscope tip section relative to its surroundings, environment or background, indicative of, for example, a use of the endoscope tip section in a typical endoscopic procedure b) an object approaches or is being brought at the predefined distance 'd' or less than that from the endoscope tip section. In one embodiment, the predefined distance 'd' is 5 centimeters.

Figure 13B:
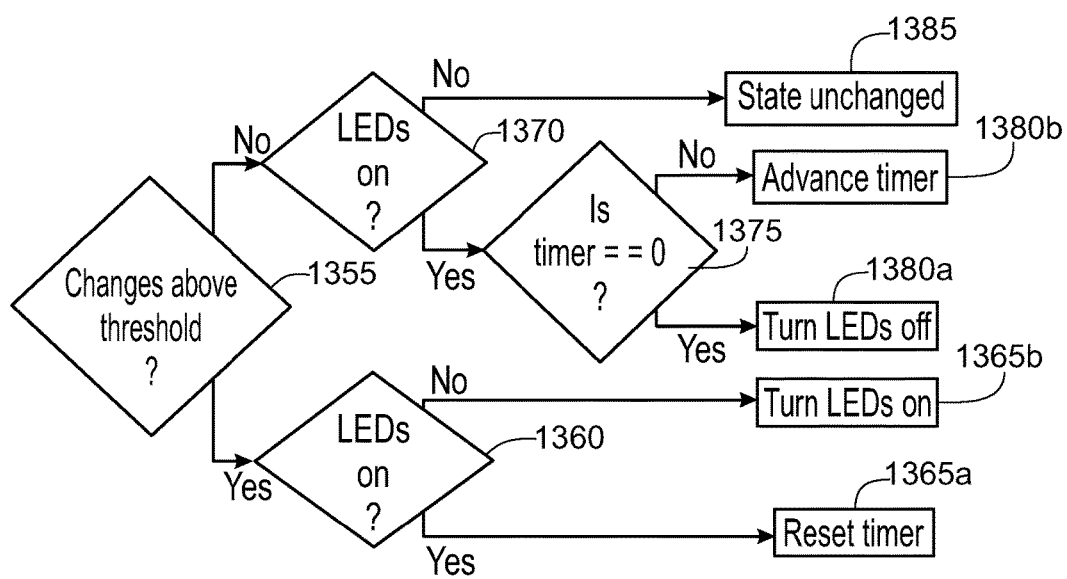
FIG. 13B is a flow chart illustrating a plurality of outcomes with reference to a decision step of the method of FIG. 13A, according to certain embodiments of the present specification.

Reference is now made to FIG. 13B which is a flow chart illustrating a plurality of additional steps and outcomes with reference to the decision step 1355 of FIG. 13A. Referring now to FIG. 13B, at step 1355 if the count or fraction of blocks, with high luminance difference or change, exceeds the second or global threshold then at step 1360 it is determined if the one or more illuminators is/are at the first intensity level which, in an embodiment, corresponds to a switched on state. If the one or more illuminators is/are at the first intensity level (i.e. in a switched on state), then at step 1365*a* a programmatic timer or counter is reset to a predefined positive integer value to allow the one or more illuminators to continue to be at the first intensity level or in the switched on state. That is, resetting the timer or counter to the positive integer value prevents the one or more illuminators from transitioning to the second intensity level, which in an embodiment corresponds to a switched off state, while the endoscope tip section is in the active state. In various embodiments, the programmatic timer or counter is a count-down timer that runs from a positive integer value to a zero value. If the one or more illuminators is/are at the second intensity level or in a switched off state, then at step 1365*b* the one or more illuminators is/are automatically changed, regulated or transitioned to be at the first intensity level or switched on state.

However, at step 1355, if the count or fraction of blocks with high luminance change do not exceed the second or global threshold then at step 1370 it is determined if the one or more illuminators is/are at the first intensity level or in switched on state. If the one or more illuminators is/are at the first intensity level or in switched on state, then at step 1375 it is determined if the programmatic timer or counter has reached the value zero. If yes, then at step 1380*a*, the one or more illuminators is/are automatically transitioned to be at the second intensity level or in switched off state. If no, then at step 1380*b* the programmatic timer or counter is advanced—that is, its value is decreased by one. In some embodiments, the positive integer value assigned to the timer or counter represents the maximum amount of predetermined time for which the one or more illuminators are allowed to stay at the first intensity level or switched on while the endoscope tip section is in the passive state. In other words, the one or more illuminators are set to be at the second intensity level or in switched off mode automatically after elapse of the predetermined time if the tip section in the passive state (that is, the count or fraction of blocks, with high luminance change, does not exceed the second or global threshold).

If, at step 1370, it is determined that the one or more illuminators is/are at the second intensity level or in a switched off state then at step 1385 the one or more illuminators are allowed to remain at such second intensity level or in a switched off state.

Referring back to FIGS. 2C and 2A, in various embodiments, the plurality of illuminators, such as the illuminators 242*a*, 242*b*, 242*c*, 252*a*, 252*b*, 272*a* and 272*b*, are connected in parallel to a power supply line. Each of the plurality of illuminators further comprises an illuminator circuit (an embodiment of which is described with reference to FIG. 14) configured to control the illuminator's illumination or luminance intensity level according to control signals, generated by the processor of the MCU 216 of FIG. 2A, using the method of FIGS. 13A, 13B. The control signals comprise instructions for switching on and off each illuminator independent from other illuminators under a specific parallel connection and for varying the intensities of each illuminator independently. In an embodiment, a maximal upper bound allowed current through each one of the plurality of illuminators is used to manage heat production in an illuminator or the endoscope's tip section, where the processor of the MCU 216 reduces currents in one or more illuminators accordingly, as a result of the implementation of the method of FIGS. 13A, 13B.

Figure 14:
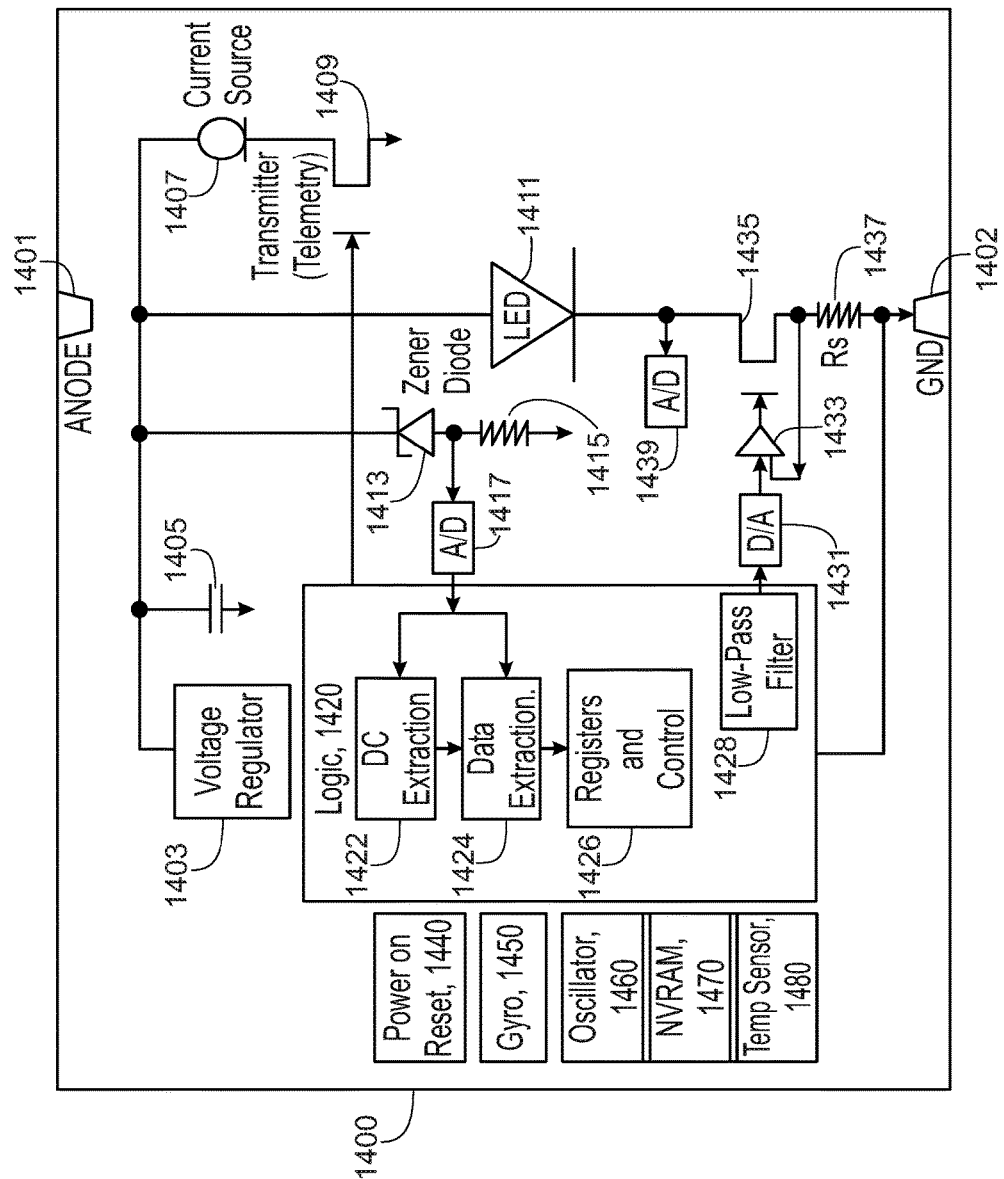
FIG. 14 is a block diagram illustrating an illuminator circuit, according to some embodiments.

Reference is now made to FIG. 14, which illustrates an illuminator circuit in a block diagram, according to certain embodiments. Illuminator circuit 1400 includes a power supply input pin ANODE 1401 on which a control signal is superimposed and a ground input pin GND 1402. ANODE pin 1401 is in electrical communication with or connected to a voltage regulator 1403, a capacitor 1405, a Zener diode 1413 and a current source 1407 which is connected further to a n-channel transistor 1409. Zener diode 1413 is in electrical communication with or connected to resistor 1415 and to analog-to-digital (A/D) converter 1417. Logic circuit 1420 receives A/D's 1417 digitized output signal, and comprises a DC extraction module 1422, a data extraction module 1424 and a registers and control module 1426. Logic circuit 1420 is configured to extract the inputted power supply DC level with the assistance of DC extraction module 1422 and to decode control signal instructions with the assistance of data extraction module 1424.

In various embodiments, data extraction module or circuit 1424 includes a UART (universal-asynchronous-receiver-transmitter) decoder that is used to decode communicated UART instructions transmitted over the power line (FIG. 15A 1550) which is connected to input pin ANODE 1401. In an embodiment, the UART protocol is a UART 9,600 bits per second protocol, includes a start bit, 1 even parity bit and 1 stop bit added to each transmitted byte.

According to various embodiments, the first UART communicated byte is an illuminator device ID, where LSB (least significant byte)=1 encodes a UART read instruction and LSB=0 encodes a UART write instruction. The second communicated byte is a 4 bit LED-enable bits and the remaining 4 bits is an accessed register address. The third communicated byte is a data byte and the fourth communicated byte is a checksum byte. Accordingly, total number of bits transmitted per one UART instruction is 44 bits. Transmitting a 44 bits UART instruction lasts 4.5 milliseconds, where 104 micro seconds is a 1 bit transmission time duration of a UART 9,600 protocol.

In an embodiment, logic circuit 1420 is implemented as an ASIC processor. However, other processor types, such as field programmable gate arrays (FPGAs), and the like, are used in certain embodiments. According to certain embodiments, logic circuit 1420 is implemented by a miniature FPGA (for example, 1.5 mm×1.5 mm FPGAs, or less, including the package are already available).

Logic circuit 1420 is configured to generate a digitized control value decoded by the UART decoder and used to determine the desired current flow through LED 411. In this example, the illuminator circuit contains just a single LED. However, in other embodiments, illuminator circuit may contain more than one LED. The digitized control value is filtered using a low pass filter logic module 1428 before it is converted to an analog signal by digital-to-analog (D/A) converter 1431 and is inputted to operational-amplifier (Op-Amp) 1433 non-inverting input. Low-pass filter 1428 is used for soft-start switching on and off LED's (1411) current gradually, minimize voltage under/over-shoot on power supply pin 1401 while LED's 1411 current is changing.

Op-Amp 1433 output is connected to the gate of an n-channel field-effect transistor (FET) 1435, whose source is connected to the inverting (feedback) input of Op-Amp 1433. A drain for FET 1435 is connected to a cathode of LED 1411 and its source to resistor (Rs) 1437. The illumination or luminance intensity, i.e. electric current flow, of LED 1411 is practically identical to that of Rs 1437. This electric current flow is controlled by Op-Amp 1433 by means of feedback: Op-Amp 1433 sets its output (hence, FET 1435 gate node) to such a voltage, that the resulting voltage at its inverting (feedback) input is identical to that of its non-inverting input which is the extracted control signal UART instruction. Hence, the resulting electric current that flows through FET 1435 and LED 1411 is configured to be the desired UART instruction's voltage divided by the resistance of Rs 1437.

Figure 15A:
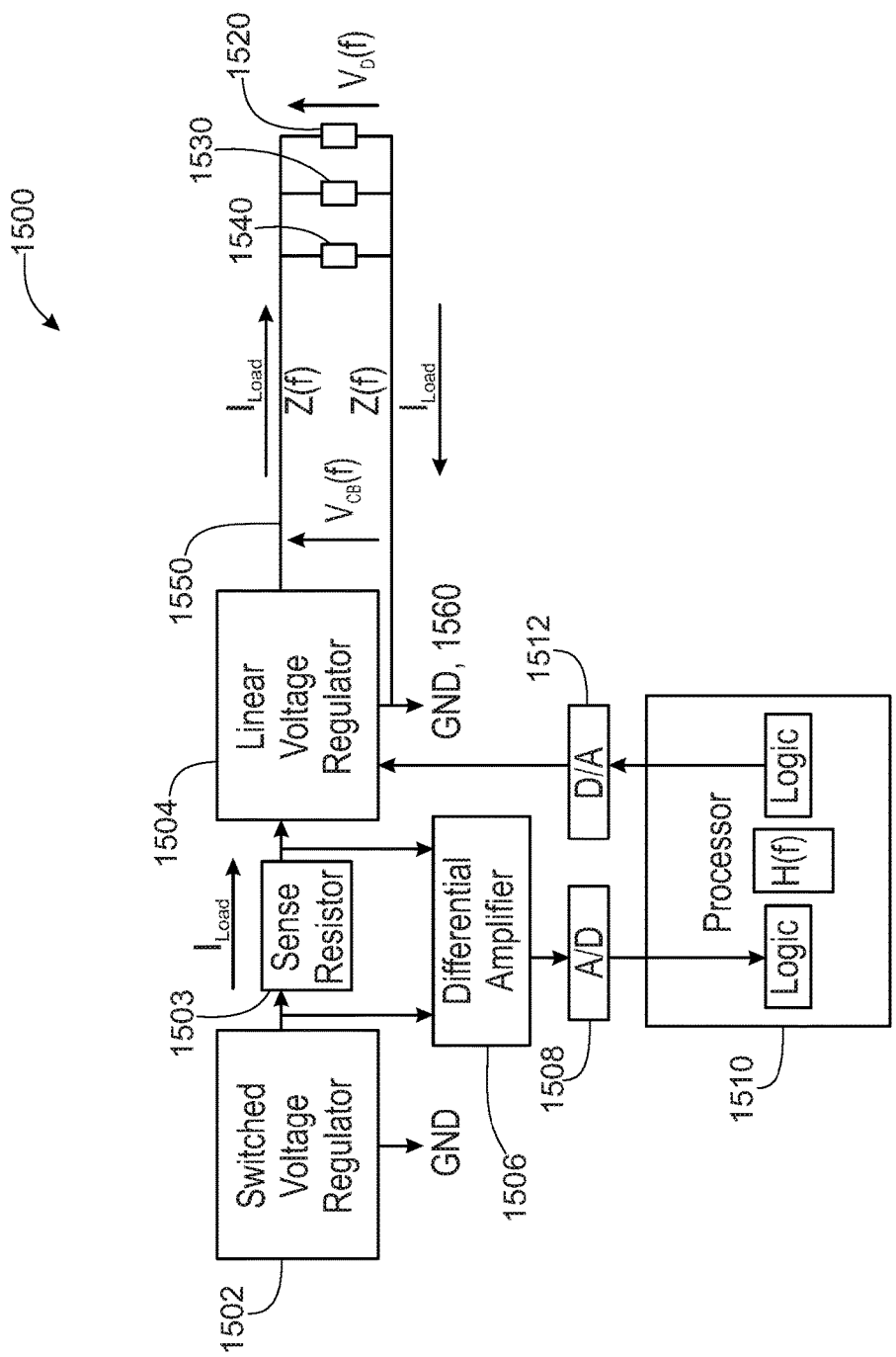
FIG. 15A is a parallel illuminating system circuit diagram, according to some embodiments.

According to certain embodiments, UART protocol is used to communicate control signal instructions over power line 1550 (see FIG. 15A). However, other standard or non-standard communication protocols, such as the serial peripheral interface (SPI) protocol, are used to communicate control signals over power line 1550 (FIG. 15A) in other embodiments.

According to certain embodiments, UART write instructions are transmitted in broadcast mode, i.e. addressing a plurality of illuminators simultaneously, and/or allowing a multiple number of LEDs to be turned on or off simultaneously.

According to certain embodiments, power line communication (PLC) known techniques, adapted to DC power, are used to modulate UART, or other communication protocol that may be used.

In an embodiment, the illuminator circuit 1400 includes power-on-reset module 1440 configured to reset logic 1420 to a known state upon power up.

In an embodiment, the illuminator circuit 1400 includes motion sensor 1450 that may be a gyro and/or an accelerometer configured to measure or maintain orientation of endoscope tip section 230 of FIG. 2C.

In an embodiment, the illuminator circuit 1400 includes oscillator 1460 configured to generate internal clock signal for illuminator circuit 1400. Frequency of oscillator 1460 may be, for example, in the range of 500 KHz to 1MHz.

In an embodiment, the illuminator circuit 1400 includes non-volatile memory cells (NVRAM) 1470 configured to store digital data such as: device parameters; illuminator part number; illuminator vendor ID; illuminator ID; records of operational hours per current range.

In an embodiment, temperature sensor 1480 is configured to measure the illuminator junction temperature at a plurality of junctions in illuminator circuit 1400, from which the endoscope tip section's equivalent temperature may be calculated.

Figure 15B:
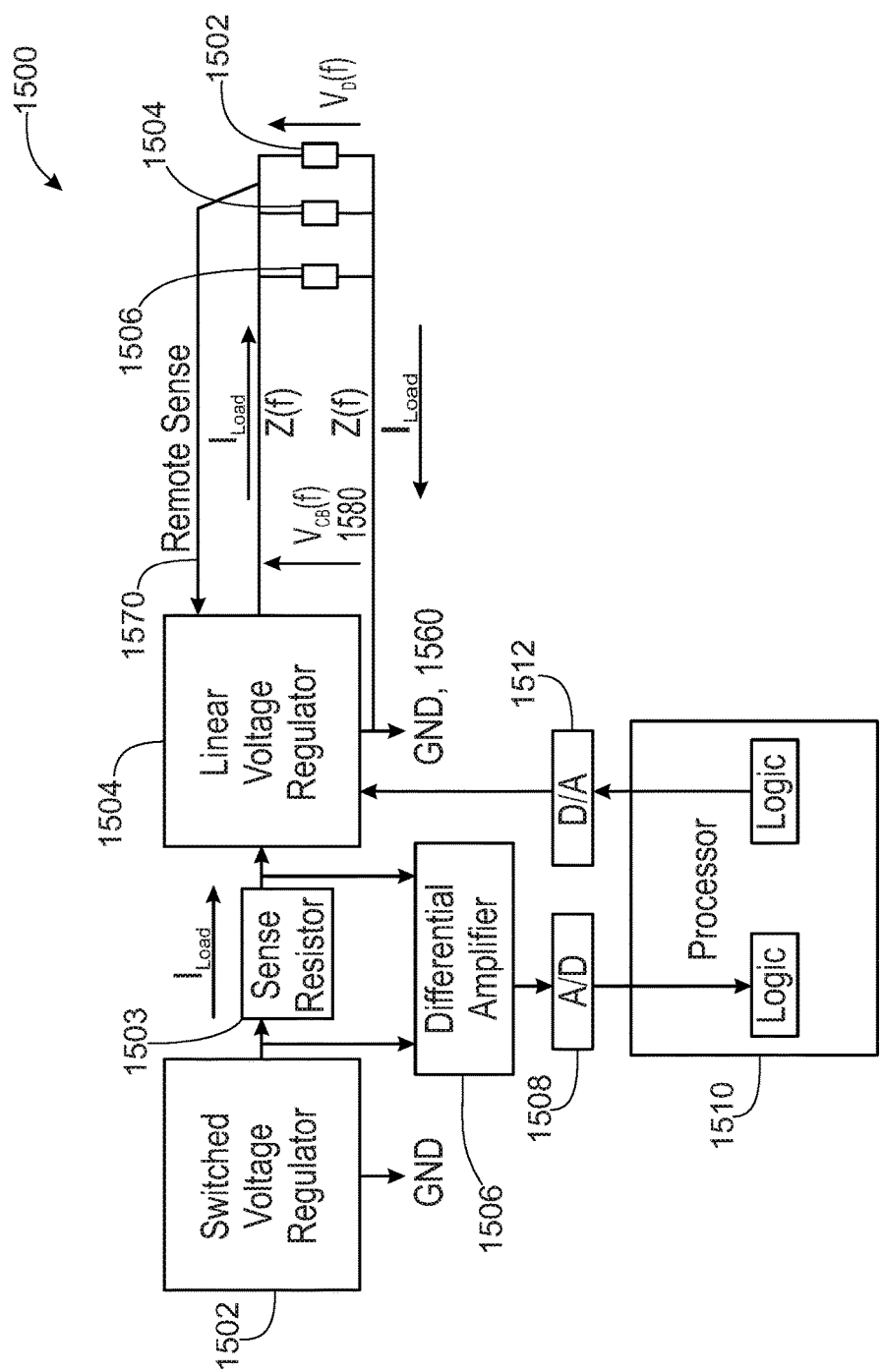
FIG. 15B illustrates the parallel illuminating system circuit diagram of FIG. 15A further incorporating a remote sense, according to some embodiments.

In an embodiment, FET 1409 switches current source 1407 (with optional soft-start), to transmit telemetry data back to processor 1510 (FIGS. 15A, 15B), in response to the instructions of processors 1510 (FIGS. 15A, 15B).

In an embodiment, A/D 1439 is configured to tap FET's 1435 drain, such that processor 1510 (FIGS. 15A, 15B), in response to a read request instruction, may be configured to determine if ANODE 1401 voltage is within a desired range (i.e. FET 1435 drain voltage is high enough such that FET 1435 functions as a current regulator, and not too high, such that FET 1435 overheats illuminator circuit 1400).

In an embodiment, illuminator circuit 1400 includes a third input pin used to communicate instructions not superimposed on power line 1550 (FIG. 15A).

Reference is now made to FIG. 15A, which illustrates a parallel illuminating system circuit, according to certain embodiments. Parallel illuminating system circuit 1500 includes switched voltage regulator 1502 current sense resistor 1503, linear voltage regulator 1504, differential amplifier 1506, A/D converter 1508, D/A converter 1512 and processor 1510. FIG. 15A is an example, in which the parallel illuminating system circuit 1500 includes three illuminator circuits 1520, 1530 and 1540 connected to single power supply line 1550. However, in actual systems the number of illuminator circuits connected to a single line may be substantially higher.

In an embodiment, the single power supply line 1550 is the camera board (CB) power supply line of an endoscope. Typically, endoscope's CB power supply line may be 3 to 4 meters long, and may carry typically 40 mA current flow per illuminator in regular (yet maximal) illumination conditions, and 150 mA current flow per illuminator in flash illumination mode. U.S. patent application Ser. No. 14/274,323 entitled "An Endoscope Tip Position Visual Indicator and Heat Management System", and filed on May 9, 2014 by the Applicant of the present specification, discloses an endoscope having a tip section equipped with multiple viewing elements, wherein each of the viewing elements' field of view is illuminated by a discrete illuminator, such as a LED, being operated in a flash mode, and is herein incorporated by reference in its entirety.

In an embodiment, the processor 1510 is a camera board (CB) circuit processor located in an external control unit (such as the MCU 216 of FIG. 2A) connected to the endoscope and to a display or in the endoscope handle.

Illuminator circuits 1520, 1530 and 1540 comprise the illuminator circuit illustrated and described with respect to FIG. 14 above wherein the power line 1550 is connected to FIG. 14 input pin ANODE 1401 and GND 1560 is connected to FIG. 14 input pin GND 1402 for each illuminator circuit 1520, 1530 and 1540. In embodiments, the processor 1510 may be an FPGA, an ASIC, a software-controlled processor and the like. In accordance with an aspect of the present specification, the processor 1510 implements the method of FIGS. 13A, 13B and is therefore a software-controlled processor. Processor 1510 is configured to generate control signal instructions (using the method of FIGS. 13A, 13B) in order to vary the illumination intensity of each illuminator 1520, 1530 and 1540 connected in parallel to power line 1550. Processor 1510 switches on or off each illuminator and regulates the illumination or luminance intensity of each illuminator independent from the operating condition of other illuminators. In an embodiment, the processor 1510 is configured to generate control signal instructions to illuminators 1520, 1530 and 1540 automatically after processing of the images captured using a plurality of viewing elements. Processor 1510 is configured to perform image processing by executing an image processing software program code (method of FIGS. 13A, 13B) stored in the processor memory. In an alternate embodiment, the processor 1510 includes an image processing hardware circuit.

In some embodiments, the processor 1510 is configured to vary the illumination intensity of illuminators 1520, 1530 and 1540 according to manual instructions of a surgeon via a user interface.

In an embodiment, processor 1510 is configured to regulate the illumination intensity of illuminators 1520, 1530 and 1540 according to the endoscope tip section's temperature calculated by measuring the temperature at the illuminator junction (using temperature sensor 1480 as shown in FIG. 14).

In an embodiment, the processor 1510 is configured to regulate the illumination intensity of illuminators 1520, 1530 and 1540 based on the feedback received from a motion sensor 1450 (FIG. 14) indications. In embodiments, motion sensor 1450 is a Micro Electro-Mechanical System (MEMS) accelerometer or gyro.

In an embodiment, processor 1510 is configured to switch on and off illuminators allocated to special operational modes, for example NBI.

In an embodiment, the processor 1510 uses the output of A/D 1508 to calculate the current flowing through power line 1550 (i.e. load current), as part of built-in test (BIT)

module whose purpose is to verify that each illuminator draws the current that it is configured to draw.

In an embodiment, the processor 1510 uses the output of A/D 1508 to calculate the current flowing through power line 1550 (i.e. load current), and then increase the output VCB of the Line Voltage Regulator 1504 to compensate for the voltage drops caused by the resistance in power line 1550 and the load current. This method of compensation is only effective if the processor 1510 is provided in advance with the value of electrical resistance of power line 1550.

In an embodiment, the processor 1510 is informed by the MCU 216 (FIG. 2A) about the resistance of power line 1550, after the MCU 216 queries the newly inserted endoscope about its type.

In an embodiment, the processor 1510 is configured to calculate the actual resistance of power line 1550, by reading from the illuminators their power supply (ANODE 1401 of FIG. 14) voltage. Accordingly, the difference between the desired VCB and the illuminators' supply voltage, divided by the current measured by the Sense Resistor (1503) and converted by A/D (1508) is the actual resistance.

According to embodiments of the present specification, more than one parallel illuminating system circuit, described in FIG. 15A hereinabove, may be implemented, thereby reducing the current load from the power line and increasing the communication throughput.

Reference is now made to FIG. 15B, which illustrates the parallel illuminating system of FIG. 15A further incorporating a remote sense, according to certain embodiments. In an embodiment, the parallel illuminating system circuit 1500 includes remote sense line 1570. In an embodiment, the remote sense line 1570 is configured to provide a measure of the actual voltage applied on the illuminators circuit inputs in order to provide the desired operational condition. In an embodiment, the remote sense line 1570 is configured to detect a voltage fall, due to supply line's 1550 load, and the processor 1510 is configured to compensate the voltage fall by increasing the applied voltage VCB 1580.

Figure 16:
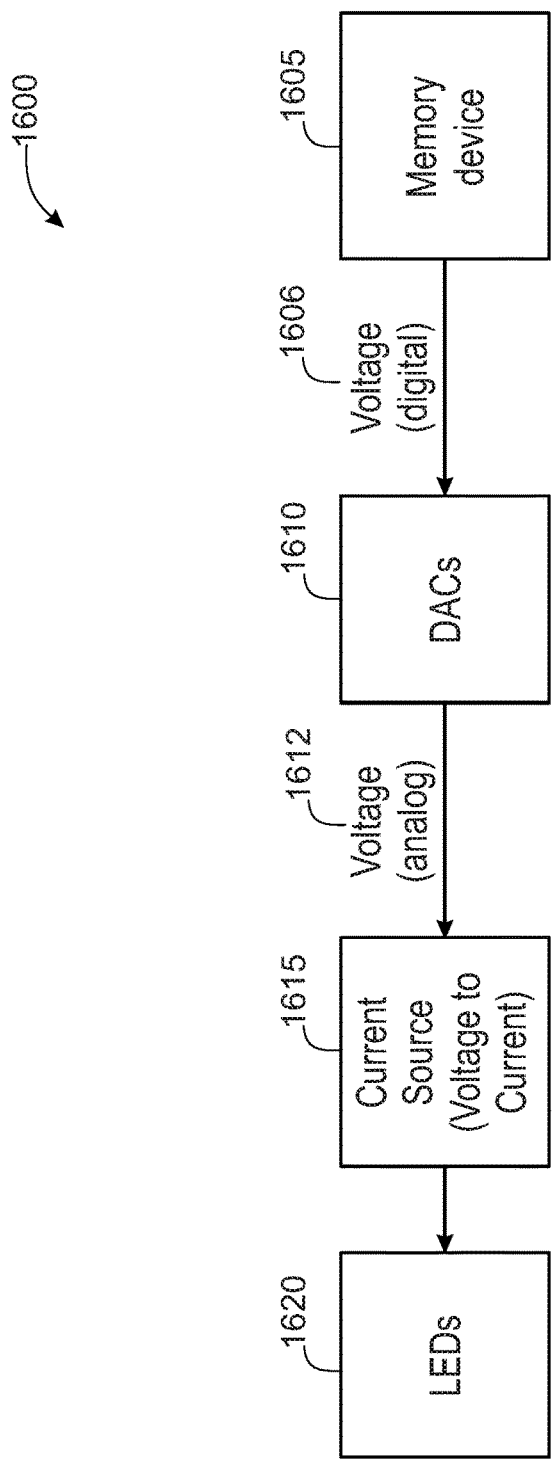
FIG. 16 is a block diagram illustrating another illuminator circuit, according to some embodiments.

FIG. 16 is a block diagram illustration of another embodiment of an illuminator circuit 1600. The circuit 1600 includes non-volatile memory cells (NVRAM) 1605 configured to store digital data such as, but not limited to, voltage data. The stored digital voltage value 1606 is applied to a digital to analog convertor 1610 that outputs a corresponding analog voltage 1612. The analog voltage 1612 is input to a voltage regulator 1615 that converts the input analog voltage 1612 to corresponding current for supplying to one or more LEDs 1620, which may be connected in series in accordance to some embodiments.

Figure 17:
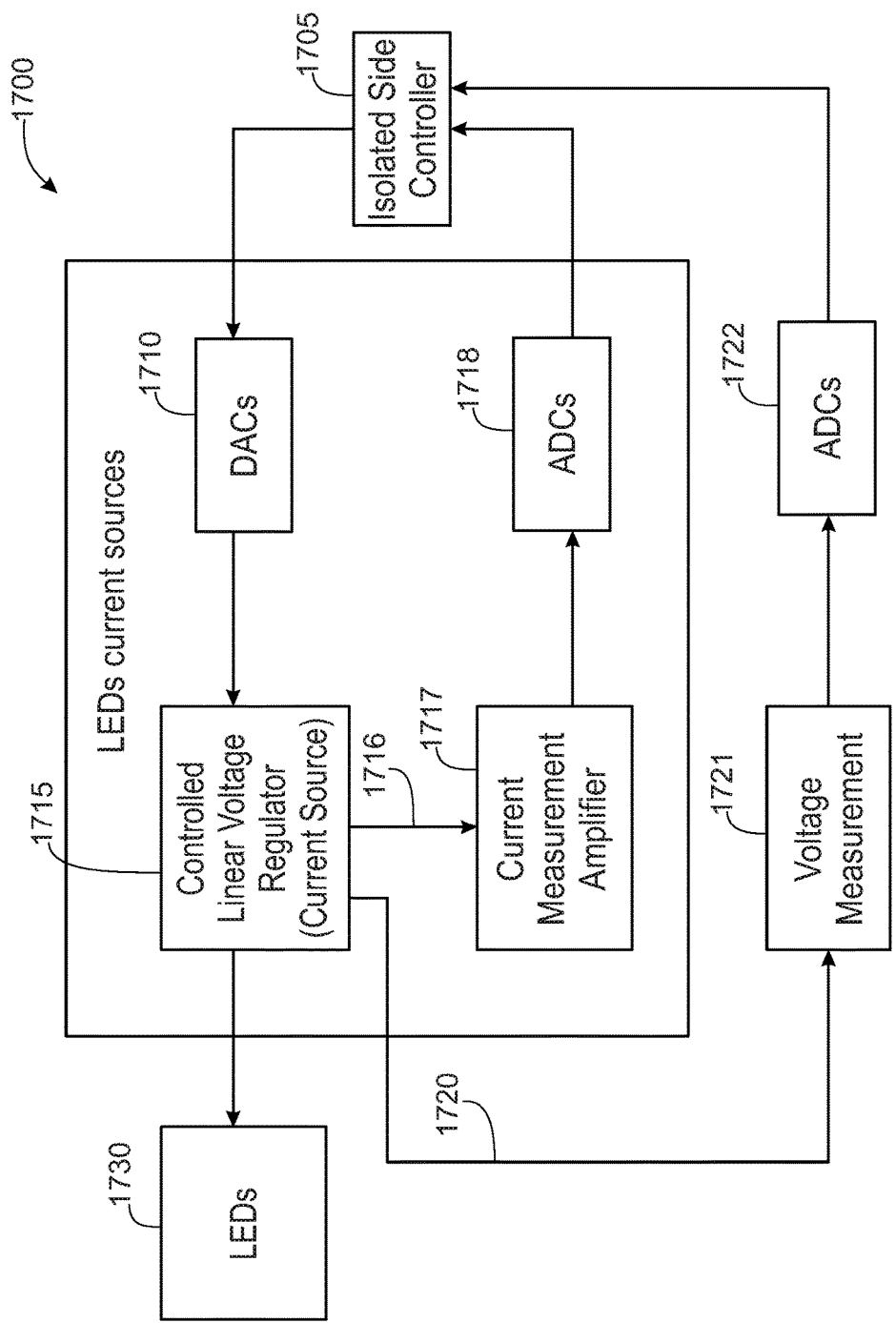
FIG. 17 is a block diagram illustrating yet another illuminator circuit, according to some embodiments.

FIG. 17 is a block diagram illustration of yet another embodiment of an illuminator circuit 1700. The circuit 1700 includes a processor 1705 which in various embodiments may be an FPGA, an ASIC, a software-controlled processor and the like. In accordance with an aspect of the present specification, the processor 1705 implements the method of FIGS. 13A, 13B and is therefore a software-controlled processor. Processor 1705 is configured to generate control signal instructions (using the method of FIGS. 13A, 13B) in order to vary the illumination intensity of one or more LEDs 1730 that may be connected in series in some embodiments. Control digital signals from the processor 1705 are received by the digital to analog converter (DAC) 1710 that converts the digital signals, such as digital voltage, into analog signals (analog voltage). The analog signals, output from the DAC 1710 are input to a voltage regulator 1715 that in turn applies an analog current to the one or more LEDs 1730. A first feedback line 1716 from the voltage regulator 1715 conveys the analog current level generated at the voltage regulator 1715 back to the processor 1705 via a current measurement amplifier 1717 and an analog to digital converter (ADC) 1718. Also, a second feedback line 1720 from the voltage regulator 1715 conveys the analog voltage level at the voltage regulator 1715 back to the processor 1705 via a voltage measurement element 1721 and an analog to digital converter (ADC) 1722.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. An endoscopy system comprising:
    an endoscope having a tip;
    a plurality of viewing elements located at the endoscope tip, wherein each of said viewing elements comprises an image sensor having a field of view illuminated by one or more light emitting diode (LED) illuminators;
    a circuit board comprising a circuit for measuring a voltage across each of said LED illuminators; and
    a controller programmed to compute a temperature of each of said LED illuminators by using said measured voltage and a function representing a relationship between LED voltage and LED junction temperature for a given current,
    wherein the controller is further programmed to compute an average of LED junction temperatures and use that average to compute the temperature at a given point on the endoscope tip, and
    wherein a relationship between the average of LED junction temperatures and the temperature at the given point on the endoscope tip is pre-determined by measuring an average LED junction temperature and a corresponding temperature at the given point on the endoscope tip for a range of LED currents and identifying a relationship between average LED junction temperatures and temperatures for the given point on the endoscope tip.

2. The system of claim 1, wherein the controller is further programmed to reduce a power of the LED illuminators if the average LED junction temperature exceeds a pre-determined limit.

3. The system of claim 1, wherein the function representing the relationship between LED voltage and LED junction temperature is pre-determined by measuring LED voltage and LED junction temperature for a range of LED currents and identifying a relationship between LED voltage and junction temperature.

4. The system of claim 1, wherein said relationship is estimated using regression analysis.

5. A method for determining a temperature in an endoscope, without using a separate, dedicated temperature sensor, wherein said endoscope comprises a plurality of viewing elements located at a distal tip of the endoscope and wherein each of said viewing elements comprises an image sensor having a field of view illuminated by one or more LED illuminators, said method comprising:
    measuring a voltage across at least one of said LED illuminators;

computing a junction temperature for the at least one of said LED illuminators by using a value of the measured voltage and a function representing a relationship between LED voltage and LED junction temperature for a given current and for the at least one of said LED illuminators; and computing an average of junction temperatures of at least two LED illuminators present in the endoscope and using that average to compute the temperature at a given point on the distal tip;

wherein an average of junction temperature of only the LED illuminators, which are directly adjacent the given point on the distal tip, are used to estimate the temperature at said given point.

6. The method of claim 5, wherein an average of junction temperatures of all the LED illuminators is used to estimate the temperature at the given point on the distal tip.

7. The method of claim 5, wherein a power of the at least one of said LED illuminator is reduced if a junction temperature of said LED illuminator exceeds a pre-determined limit.

8. The method of claim 5, wherein the function representing the relationship between LED voltage and LED junction temperature is pre-determined by measuring LED voltage and LED junction temperature for a range of LED currents and identifying a relationship between the LED voltage and LED junction temperature.

9. The method of claim 5, wherein a relationship between average LED junction temperature and the temperature at said given point on the distal tip is pre-determined by measuring average LED junction temperature and the temperature at a given point on the distal tip for a range of LED currents and identifying a relationship between the average LED junction temperature and the temperature at the given point.

10. A method for determining a temperature in an endoscope, wherein said endoscope comprises a plurality of viewing elements located in a distal tip of the endoscope and wherein each of said viewing elements comprises an image sensor having a field of view illuminated by one or more LED illuminators, said method comprising:

measuring a voltage across at least one of said LED illuminators; and computing a junction temperature for the at least one of said LED illuminators by using a value of the measured voltage and a function representing a relationship between LED voltage and LED junction temperature for the at least one of said LED illuminators, wherein the function representing the relationship between LED voltage and LED junction temperature is pre-determined by measuring LED voltage and LED junction temperature for a range of LED currents and identifying a relationship between the LED voltage and LED junction temperature.

* * * * *